United States Patent
Tearney et al.

(10) Patent No.: US 11,147,503 B2
(45) Date of Patent: Oct. 19, 2021

(54) SYSTEMS AND METHODS FOR AN ACTIVELY CONTROLLED OPTICAL IMAGING DEVICE

(71) Applicant: The General Hospital Corporation, Boston, MA (US)

(72) Inventors: Guillermo J. Tearney, Cambridge, MA (US); Rohith K. Reddy, Boston, MA (US); Michalina J. Gora, Klingenthal (FR); Kengyeh K. Chu, Boston, MA (US); Matthew Beatty, Boston, MA (US); Jing Dong, Malden, MA (US); Emilie Beaulieu-Ouellet, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 541 days.

(21) Appl. No.: 15/882,557

(22) Filed: Jan. 29, 2018

(65) Prior Publication Data

US 2018/0160965 A1 Jun. 14, 2018

Related U.S. Application Data

(63) Continuation-in-part of application No. PCT/US2016/054772, filed on Sep. 30, 2016.
(Continued)

(51) Int. Cl.
*A61B 5/00* (2006.01)
*A61B 1/06* (2006.01)
(Continued)

(52) U.S. Cl.
CPC ........ *A61B 5/4255* (2013.01); *A61B 1/00006* (2013.01); *A61B 1/00096* (2013.01);
(Continued)

(58) Field of Classification Search
CPC combination set(s) only.
See application file for complete search history.

(56) References Cited

U.S. PATENT DOCUMENTS

| 3,629,677 A | 12/1971 | Means |
| 5,193,526 A | 3/1993 | Daikuzono |

(Continued)

FOREIGN PATENT DOCUMENTS

| CN | 102499617 A | 6/2012 |
| CN | 103052368 A | 4/2013 |

(Continued)

OTHER PUBLICATIONS

International Search Report and Written Opinion issued in corresponding International Application No. PCT/US16/54772 dated Jan. 6, 2017, 21 pages.
(Continued)

*Primary Examiner* — John P Leubecker
*Assistant Examiner* — Shankar Raj Ghimire
(74) *Attorney, Agent, or Firm* — Quarles & Brady LLP

(57) ABSTRACT

Systems and methods for a tethered optical imaging probe configured to be integrated into an optical system for medical diagnosis are provided. In one configuration, the present disclosure provides a tethered optical imaging probe including a motor arranged within a swallowable capsule. A rotational speed of the motor is actively controlled by a feedback signal.

26 Claims, 19 Drawing Sheets

Related U.S. Application Data

(60) Provisional application No. 62/451,362, filed on Jan. 27, 2017, provisional application No. 62/235,175, filed on Sep. 30, 2015.

(51) Int. Cl.
  *A61B 1/00* (2006.01)
  *A61B 1/04* (2006.01)

(52) U.S. Cl.
  CPC ...... *A61B 1/00179* (2013.01); *A61B 1/00183* (2013.01); *A61B 1/041* (2013.01); *A61B 1/0615* (2013.01); *A61B 1/0653* (2013.01); *A61B 1/0661* (2013.01); *A61B 5/0071* (2013.01); *A61B 5/0084* (2013.01); *A61B 5/6861* (2013.01)

(56) References Cited

U.S. PATENT DOCUMENTS

| | | | |
|---|---|---|---|
| 5,286,922 A | 2/1994 | Curtiss | |
| 2003/0023150 A1* | 1/2003 | Yokoi | A61B 1/00032 600/300 |
| 2003/0067227 A1 | 4/2003 | Kitamura et al. | |
| 2003/0102884 A1* | 6/2003 | Sato | H02P 6/12 318/801 |
| 2005/0143644 A1* | 6/2005 | Gilad | A61B 1/045 600/407 |
| 2007/0177152 A1* | 8/2007 | Tearney | A61B 5/0084 356/477 |
| 2007/0274650 A1* | 11/2007 | Tearney | A61B 5/0066 385/118 |
| 2007/0299309 A1 | 12/2007 | Seibel et al. | |
| 2008/0021275 A1* | 1/2008 | Tearney | A61B 5/0084 600/115 |
| 2008/0262312 A1 | 10/2008 | Carroll | |
| 2009/0137876 A1* | 5/2009 | Brophy | A61B 5/061 600/167 |
| 2010/0245549 A1* | 9/2010 | Allen | A61B 1/00193 348/65 |
| 2011/0218403 A1* | 9/2011 | Tearney | A61B 5/0066 600/165 |
| 2012/0022338 A1* | 1/2012 | Subramaniam | A61B 5/0086 600/301 |
| 2013/0063964 A1 | 3/2013 | Meir et al. | |
| 2013/0080119 A1* | 3/2013 | Khait | A61B 5/065 702/194 |
| 2013/0310643 A1* | 11/2013 | Gora | A61B 1/041 600/109 |
| 2013/0345510 A1 | 12/2013 | Hadani | |
| 2014/0155753 A1 | 6/2014 | McGuire, Jr. et al. | |
| 2014/0155783 A1* | 6/2014 | Starksen | A61M 25/0054 600/585 |
| 2015/0182190 A1* | 7/2015 | Hiltner | A61B 34/30 600/463 |
| 2015/0208539 A1* | 7/2015 | Blunier | A61B 1/0661 312/223.1 |
| 2016/0345809 A1* | 12/2016 | Tearney | A61B 1/00147 |
| 2017/0027417 A1* | 2/2017 | Kawai | A61B 1/0016 |
| 2017/0273542 A1* | 9/2017 | Au | A61B 1/00006 |
| 2018/0372477 A1* | 12/2018 | Elmaanaoui | G01B 9/02001 |

FOREIGN PATENT DOCUMENTS

| | | |
|---|---|---|
| CN | 204204473 U | 3/2015 |
| WO | 2009102445 A2 | 8/2009 |
| WO | 2013177154 A1 | 11/2013 |
| WO | 2015020124 A1 | 2/2015 |
| WO | 2015072432 A1 | 5/2015 |

OTHER PUBLICATIONS

China National Intellectual Property Administration. Notice on the First Office Action. dated Aug. 1, 2019. With translation.
China National Intellectual Property Administration. Notice on the Second Office Action. dated May 18, 2020. With translation.
European Patent Office. Extended European Search Report for application 16852710.9. dated May 21, 2019.

* cited by examiner

SYSTEMS AND METHODS FOR AN ACTIVELY CONTROLLED OPTICAL IMAGING DEVICE

CROSS-REFERENCES TO RELATED APPLICATIONS

The present disclosure is based on, and claims the benefit of U.S. Provisional Patent Application No. 62/451,362, filed Jan. 27, 2017, and entitled "Structured Tethered Capsule Endomicroscopy for Imaging Lumal Organs," and is a continuation-in-part of International Patent Application No. PCT/US2016/054772, filed Sep. 30, 2016, and entitled "Systems and Methods for an Actively Controlled Optical Imaging Device," which claims the benefit of U.S. Provisional Patent Application No. 62/235,175, filed Sep. 30, 2015, and entitled "Actively Controlled Optical Imaging Device." Each of the foregoing applications is hereby incorporated herein by reference in its entirety for all purposes.

STATEMENT REGARDING FEDERALLY SPONSORED RESEARCH

This invention was made with government support under CA184102 awarded by the National Institutes of Health and DK100569 awarded by the National Institutes of Health. The government has certain rights in the invention.

BACKGROUND

The disclosure relates generally to optical imaging systems and, more specifically, to optical imaging systems utilizing a tethered optical imaging probe for medical diagnosis.

Tethered optical imaging devices are used in some medical imaging applications in an attempt to replace more invasive medical procedures. For example, diagnosis of diseases in the gastrointestinal (GI) tract, which are typically diagnosed by an endoscopy where a patient is anesthetized, may be carried out via a tethered optical imaging device that is swallowed by a patient.

A current tethered optical imaging device 10 is illustrated in FIG. 1. As shown in FIG. 1, the tethered optical imaging device 10 includes a rotary junction 12 coupled to a capsule 14 by a sheath 16. The rotary junction 12 is a fixed component of the optical imaging device 10 (i.e., non-disposable and required) that presents a significant cost (e.g., ~$10,000). The significant cost of the rotary junction 12 results from the complexity of the component. That is, the rotary junction 12 includes a motor 18 and a plurality of optics 20 arranged within the rotary junction 12. Some of the plurality of optics 20 are rotatably coupled to the motor 18 for rotation therewith. The motor 18 is also rotatably coupled to an optical fiber 22 that is arranged within the sheath 16 and extends into the capsule 14.

The design of the current tethered optical imaging device 10 may lead to various complexities and deficiencies associated with the device. For example, some of the plurality of optics 20 are required to rotate within the rotary junction 12, which requires additional components to facilitate transmitting light therethrough. The sheath 16 is required to define a larger diameter in order to accommodate the rotating optical fiber 22 therein. The mechanical properties of the sheath 16 and optical fiber 22 must provide a low friction between the two components to ensure proper operation. Additionally, the optical properties (e.g., transmission efficiency, beam profile, etc.) of the rotating optical fiber 22 may change as the sheath is bent during operation.

Due to the deficiencies in current tethered optical imaging devices, it would be desirable to have a tethered optical imaging probe that is easily integrated into an optical system and that is fabricated entirely of low-cost, disposable components.

BRIEF SUMMARY

The present disclosure provides systems and methods for a tethered optical imaging probe configured to be integrated into an optical system for medical diagnosis. In one configuration, the present disclosure provides a tethered optical imaging probe including a motor arranged within swallowable capsule. A rotational speed of the motor is actively controlled by a feedback signal.

In one aspect, the present disclosure provides a tethered optical imaging probe including a motor, a reflective surface rotatably coupled to the motor, and a capsule enclosing the motor and the reflective surface. The capsule is dimensioned to be swallowable by a patient. The tethered optical imaging probe further includes a tether coupled to a first end of the capsule. The tether includes an optical waveguide arranged therein. The optical waveguide is arranged to receive source light at a distal end of the optical waveguide and project the source light from a proximal end of the optical waveguide onto the reflective surface and/or to receive reflected light from the reflective surface at the proximal end of the optical waveguide and transmit the reflected light to the distal end of the optical waveguide.

In one aspect, the present disclosure provides a tethered capsule endomicroscopy system including an optical source arranged to emit source light, and an optical imaging probe. The optical imaging probe includes a motor, a reflective surface rotatably coupled to the motor, and a capsule enclosing the motor and the reflective surface. The capsule is dimensioned to be swallowable by a patient. The optical imaging probe further includes a tether coupled to a first end of the capsule. The tether includes an optical waveguide arranged therein. The optical waveguide is arranged to receive the source light at a distal end of the optical waveguide and project the source light from a proximal end of the optical waveguide onto the reflective surface and/or to receive reflected light from the reflective surface at the proximal end of the optical waveguide and transmit the reflected light to the distal end of the optical waveguide. The tethered capsule endomicroscopy system further includes an optical detector arranged to detect the reflected light from the reflective surface transmitted to the distal end of the optical waveguide, and a controller configured to reconstruct the reflected light detected by the optical detector into cross-sectional morphological data.

In one aspect, the present disclosure provides an optical imaging system including a tethered optical imaging probe. The tethered optical imaging probe includes a motor coupled to an optical component and configured to selectively rotate the optical component at a rotational speed, and a capsule enclosing the motor and the optical component. The capsule is dimensioned to be swallowable by a patient. The tethered optical imaging probe further includes a detection object arranged within the capsule, and a tether coupled to a first end of the capsule. The tether includes an optical waveguide arranged therein. A signal is generated as the optical component is rotatably positioned by the motor to direct emitted light from the detection object to the optical waveguide. The optical imaging system further includes a controller in communication with the motor and configured to control the rotational speed of the motor to a desired rotational speed based on feedback from the signal.

In one aspect, the present disclosure provides an optical imaging system including an optical source arranged to emit source light, and an optical imaging probe. The optical imaging probe includes a motor, a reflective surface rotatably coupled to the motor, and a capsule enclosing the motor and the reflective surface. The capsule is dimensioned to be swallowable by a patient. The optical imaging probe further includes a detection object arranged within the capsule, and a tether coupled to a first end of the capsule. The tether includes an optical waveguide arranged therein. The optical waveguide is arranged to receive the source light at a distal end of the optical waveguide and project the source light from a proximal end of the optical waveguide onto the reflective surface and/or to receive reflected light from the reflective surface at the proximal end of the optical waveguide and transmit the reflected light to the distal end of the optical waveguide. A signal is generated as the reflective surface is rotatably positioned by the motor to direct emitted light from the detection object to the proximal end of the optical waveguide for transmission to the distal end of the optical waveguide. The optical imaging system further includes an optical detector arranged to detect the reflected light from the reflective surface transmitted to the distal end of the optical waveguide, and a controller in communication with the motor and configured to reconstruct the reflected light detected by the detector into cross-sectional morphological data. The controller is further configured to control a rotational speed of the motor to a desired rotational speed based on feedback from the signal.

In one aspect, the present disclosure provides a method for controlling a tethered optical imaging probe. The tethered optical imaging probe includes a motor, a reflective surface rotatably coupled to the motor, a capsule enclosing the motor and the reflective surface, and a tether coupled to a first end of the capsule and having an optical waveguide arranged therein. The tethered optical imaging probe further includes a detection object arranged within the capsule. The capsule is dimensioned to be swallowable by a patient. The optical waveguide is arranged to receive source light at a distal end of the optical waveguide and project the source light from a proximal end of the optical waveguide onto the reflective surface and/or to receive reflected light from the reflective surface at the proximal end of the optical waveguide and transmit the reflected light to the distal end of the optical waveguide. The method includes outputting source light from the optical waveguide onto the reflective surface, and rotating the reflective surface, via the motor, thereby forming a circumferential optical path formed by the source light output from the optical waveguide onto the reflective surface as the reflective surface is rotated. The detection object is arranged in the circumferential optical path. The method further includes generating a signal each time the reflective surface directs light emitted from the detection object to the proximal end of the optical waveguide, and controlling a rotational speed of the motor using the generated signal.

In one aspect, the present disclosure provides a method for controlling a tethered optical imaging probe. The tethered optical imaging probe includes a motor, a reflective surface rotatably coupled to the motor, a capsule enclosing the motor and the reflective surface, and a tether coupled to a first end of the capsule and having an optical waveguide arranged therein. The tethered optical imaging probe further includes a light emitting object arranged within the capsule. The capsule is dimensioned to be swallowable by a patient. The optical waveguide is arranged to receive reflected light from the reflective surface at the proximal end of the optical waveguide and transmit the reflected light to the distal end of the optical waveguide. The method includes rotating the reflective surface, via the motor, thereby forming a circumferential field of view in which emitted light is periodically directed to the reflective surface and reflected to the proximal end of the optical waveguide as the reflective surface is rotated. The light emitting object is arranged in the circumferential field of view. The method further includes generating a signal each time the reflective surface directs light emitted from the light emitting object to the proximal end of the optical waveguide, and controlling a rotational speed of the motor using the generated signal.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

Figure 2:
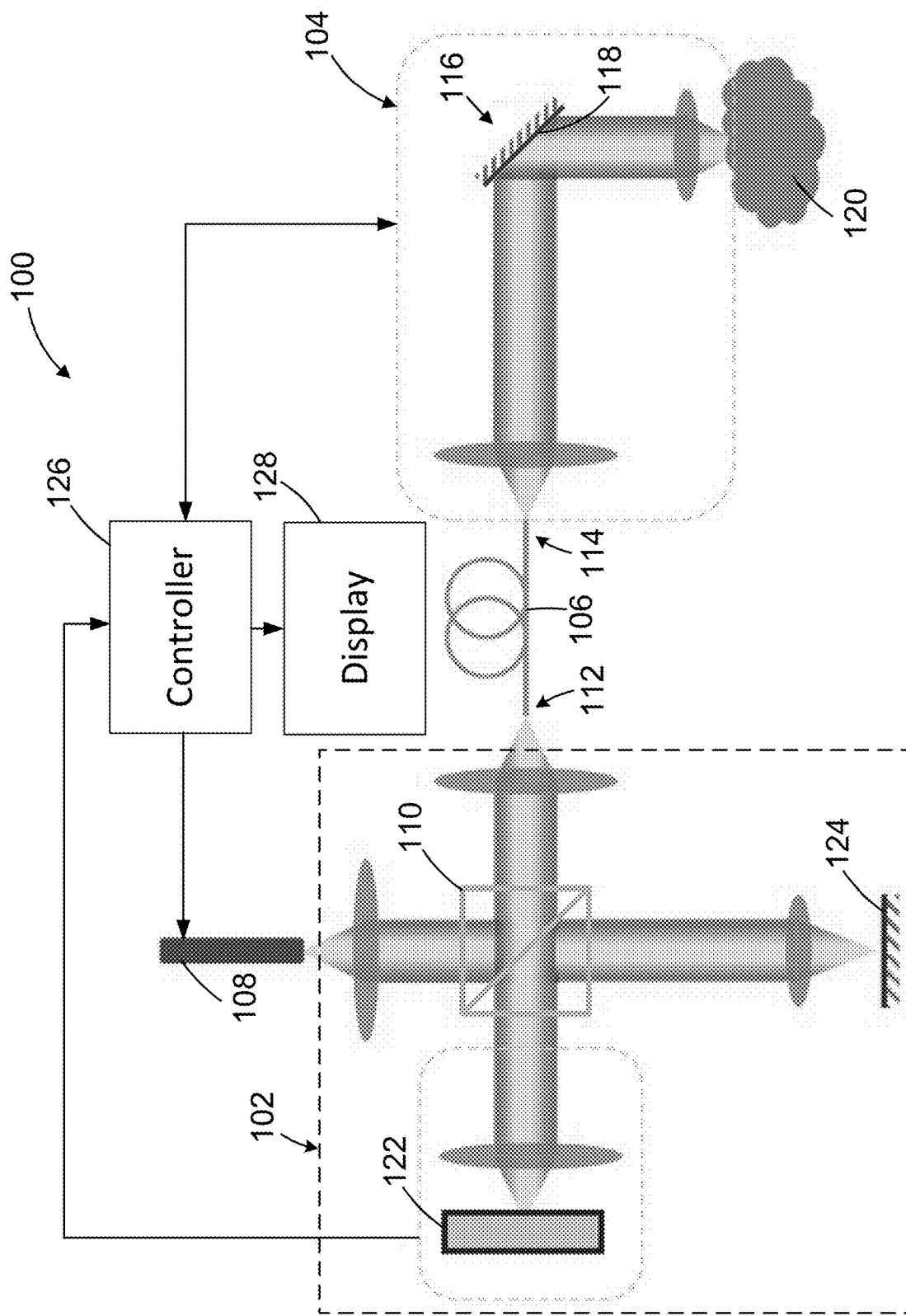
FIG. 2 is a schematic illustration of an optical imaging system according to one aspect of the present disclosure.

FIG. 2 illustrates one non-limiting example of an optical system 100 according to the present disclosure. The optical system 100 includes an external optical assembly 102 optically coupled to a tethered optical imaging probe 104 via an optical waveguide 106. The external optical assembly 102 is configured to receive source light from a light source 108, and includes a beam splitter 110 to reflect the source light into a distal end 112 of the optical waveguide 106. In some non-limiting examples, the light source 108 may be in the form of a broadband laser configured to sweep wavelengths in the near-infrared spectrum.

The optical waveguide 106 is configured to efficiently transmit the source light along the optical waveguide 106 from the distal end 112 to a proximal end 114 of the optical waveguide 106. The proximal end 114 of the optical waveguide 106 is coupled to the tethered optical imaging probe 104 and arranged to project the source light from the proximal end 114 onto an optical component 116 within the tethered optical imaging probe 104.

The illustrated optical component 116 is in the form of a reflective surface 118 configured to efficiently reflect the source light emitted from the proximal end 114 of the optical waveguide 106 onto a sample 120 (e.g., a portion of a luminal organ or tissue within a patient). The proximal end 114 of the optical waveguide 106 is arranged to receive reflected light from the sample 120 off of the reflective surface 118. The reflected light is transmitted along the optical waveguide 106 from the proximal end 114 to the distal end 112. In some non-limiting examples, the optical waveguide 106 may be in the form of an optical fiber, an optical fiber bundle, a plurality of optical fibers, or other structures known by those having ordinary skill in the optical arts to be suitable for use as an optical waveguide 106. It should be appreciated that the optical waveguide 106 is not limited to a single optical fiber that performs both transmission of the source light and the reflected light from the sample 120. That is, in some non-limiting examples, the optical waveguide 106 may comprise a fiber bundle where a core is arranged to transmit one of the source light or the reflected light from the sample 120 and surrounding fibers are arranged to transmit the other of the source light or the reflected light from the sample 120. In other non-limiting examples, the optical waveguide 106 may comprise two totally separate fibers one for transmitting source light to the reflective surface 118 and another for transmitting reflected light from the sample 120.

The reflected light from the sample 120 transmitted to the distal end 112 of the optical waveguide 106 transmits through the beam splitter 110 to an optical detector 122. In some non-limiting examples, the optical detector 122 may be in the form of a CCD array, a CMOS array, photodiodes (made of Silicon, Germanium, InGaAs, Lead sulfide, or other materials), photocells, photoresistors, phototransistors or other photosensors. A portion of the source light output by the light source 108 transmits through the beam splitter 110 to a reference mirror 124. The portion of the source light incident on the reference mirror 124 reflects off the reference mirror 124 and is directed by the beam splitter 110 to the optical detector 122. Thus, in operation, the optical detector 122 receives both reference source light reflected from the reference mirror 124 and reflected light off the reflective surface 118 from the sample 120.

A controller 126 is in communication with the tethered optical imaging probe 104, the light source 108, the optical detector 122, and a display 128. The controller 126 may be in wired communication (e.g., via Ethernet, USB, CAN, etc.) with the tethered optical imaging probe 104, the light source 108, the optical detector 122, and/or the display 128. Alternatively or additionally, the controller 126 may be in wireless communication (e.g., via Bluetooth®, WiFi, etc.) with the tethered optical imaging probe 104, the light source 108, the optical detector 122, and/or the display 128.

The controller 126 is configured to control the operation of the tethered optical imaging probe 104, as will be described below. The controller 126 is further configured to reconstruct the reflected light off the reflective surface 118 from the sample 120 that is detected by the optical detector 122 into cross-sectional morphological data. In one non-limiting example, the optical system 100 is configured to implement an optical frequency domain imaging technique to generate the cross-sectional morphological data. Sequential cross-sections may also be compiled to reconstruct a three-dimensional representation, for example, of an entire luminal organ of a patient.

Figure 3:
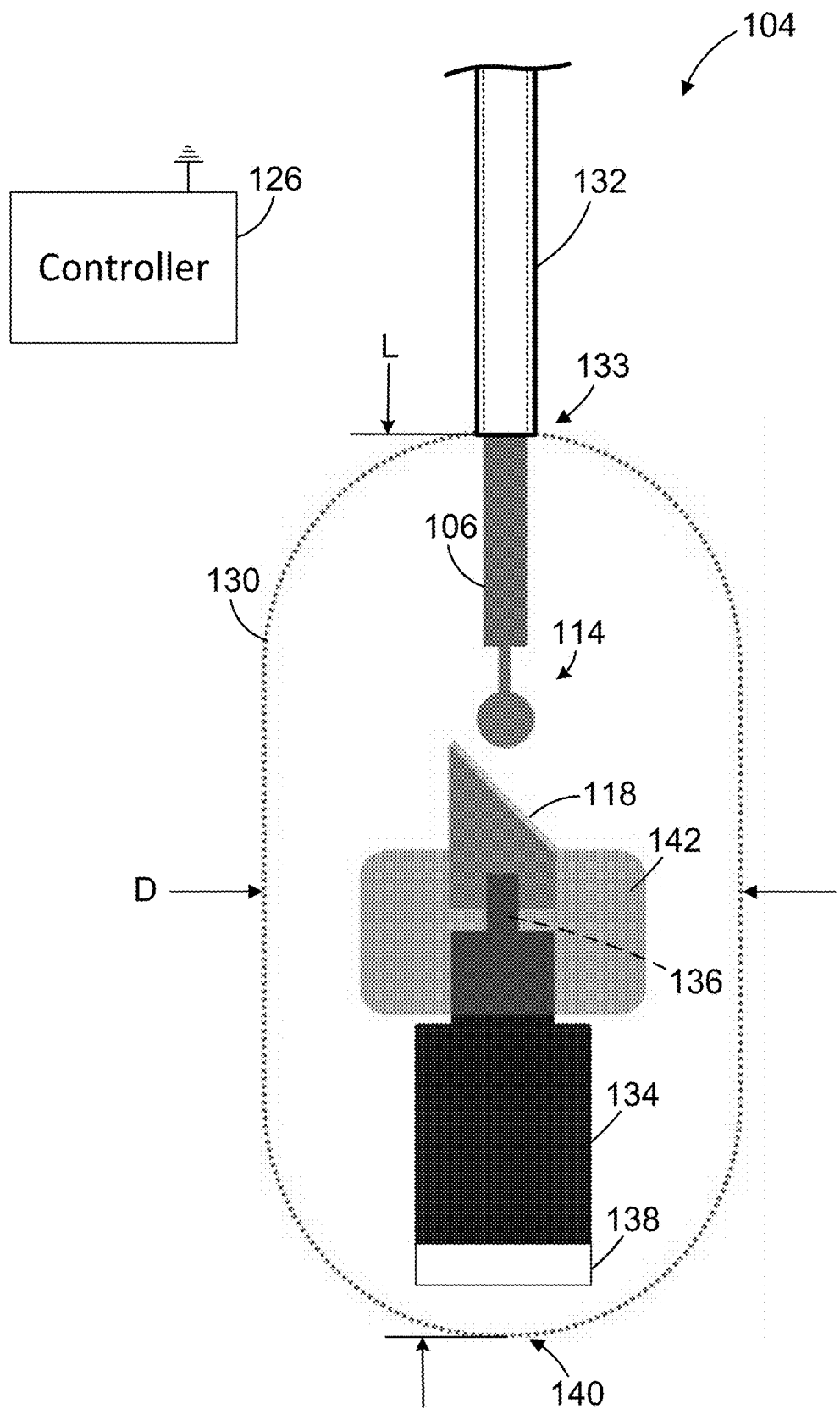
FIG. 3 is a schematic illustration of a wireless tethered optical imaging probe of the optical system of FIG. 2 according to one aspect of the present disclosure.

FIG. 3 illustrates one non-limiting example of the tethered optical imaging probe 104 according to the present disclosure. The tethered optical imaging probe 104 includes a capsule 130 and a tether 132 coupled to a first end 133 of the capsule 130. The capsule 130 is dimensioned to be swallowable by a patient, which can be in certain cases, a human patient such as an adult or a child patient, and which can be in other cases, a veterinary patient. The capsule 130 defines a generally cylindrical shape with hemispherical ends. The capsule 130 defines a capsule diameter D and a capsule length L. In some non-limiting examples, the capsule diameter D may be between approximately 5 millimeters (mm) and approximately 20 mm. In other non-limiting examples, the capsule diameter D may be between approximately 10 mm and approximately 15 mm. In some non-limiting examples, the capsule length L may be between approximately 20 mm and approximately 30 mm. In other non-limiting examples, the capsule length L may be between approximately 22 mm and approximately 28 mm.

The capsule 130 is fabricated from a biocompatible material configured to efficiently transmit the source light reflected from the reflective surface 118 through the capsule 130 onto the sample 120 and to efficiently transmit the reflected light from the sample 120 through the capsule 130 onto the reflective surface 118. In some non-limiting examples, the capsule 130 may be fabricated from PMMA in combination with other plastics or metals like stainless steel or brass.

The tether 132 includes the optical waveguide 106 arranged therein. As will be described, the design of the tethered optical imaging probe 104 negates the need to rotate the optical waveguide 106. The tether 132 may define a substantially reduced diameter when compared to the sheath 16 of the prior art device 10, and does not need to be fabricated from low-friction materials to compensate for a rotating optical fiber. Thus, the tether 132 provides better flexibility and a substantially reduced cost (e.g., ~$0.01 compared to ~$200) when compared to the sheath 16 of the prior art device 10. The tether 132 is fabricated from a biocompatible material (e.g., Polyimide, Pebax, PTFE, FEP).

A motor 134 and the reflective surface 118 are enclosed within the capsule 130. The motor 134 includes a drive shaft 136 that rotatably couples the reflective surface 118 to the motor 134. In operation, as the motor 134 rotates the drive shaft 136, the reflective surface 118 rotates with the drive shaft 136. In the illustrated non-limiting example, the motor 134 is powered by a power supply 138 arranged within the capsule 130. The power supply 138 may be in the form of a battery, a rechargeable battery, a solar cell, etc. In the illustrated non-limiting example, the controller 126 is configured to wirelessly communicate with the motor 134. As will be described, the controller 126 is configured to supply a periodic control signal to the motor 134 to control a rotational speed of the motor.

The motor 134 is arranged within the capsule 130 such that the drive shaft 136 extends toward the first end 133 of the capsule 130, thereby arranging the reflective surface 118 rotatably coupled thereto adjacent to the proximal end 114 of the optical waveguide 106. In other non-limiting examples, the motor 134 may be rearranged to extend toward a second end 140 of the capsule opposite the first end 133. That is, the directional orientation of the motor 134, the proximal end 114 of the optical waveguide 106, and the reflective surface 118 within the capsule 130 is not meant to be limiting in any way and may be arranged differently as would be appreciated by one of skill in the art.

The motor 134 utilized in the tethered optical imaging probe 104 is disposable and low-cost (e.g., between ~$1 and $10). In one non-limiting example, the motor 134 may be a cell phone motor typically used to generate vibrations in a cell phone. Low-cost motors are generally incapable of being utilized in high precision imaging applications; however, the present disclosure provides an approach to accurately and precisely control the motor 134 to facilitate the acquisition of high quality imaging data, as will be described. Due to the low cost of the components used to manufacture the tethered optical imaging probe 104, the tethered optical imaging probe 104 may entirely disposable after use without an end user sustaining significant costs.

The drive shaft 136 of the motor 134 may include a damping weight 142 coupled thereto for rotation therewith. As will be described, the damping weight 142 reduces short-term fluctuations in a rotational speed of the motor 134 by increasing a moment of inertia. The damping weight 142 defines a generally cylindrical shape. The damping weight 142 may be fabricated from a metal material (e.g., brass). In some non-limiting examples, the damping weight 142 may define a weight of between approximately 0.01 grams (g) and 4 g.

Figure 4:
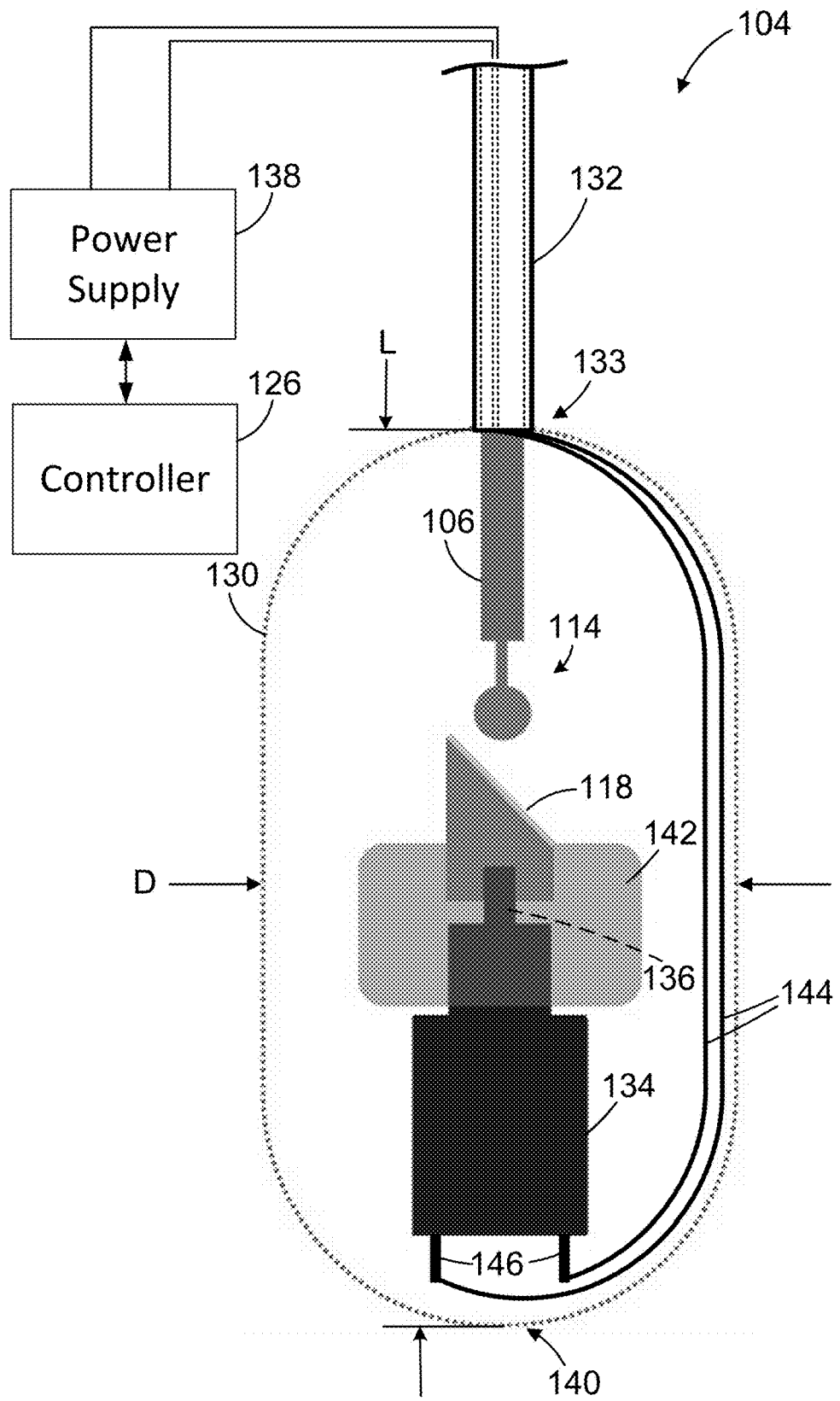
FIG. 4 is a schematic illustration of a wired tethered optical imaging probe of the optical system of FIG. 2 according to another aspect of the present disclosure.

FIG. 4 illustrates another non-limiting example of the tethered optical imaging probe 104 according to the present disclosure. The tethered optical imaging probe 104 of FIG. 4 is similar to the tethered optical imaging probe 104 of FIG. 3, except as described below or as shown in the figures. Similar components are identified using like reference numerals. As shown in FIG. 4, the tethered optical imaging probe 104 includes one or more wires 144 extending into and along the capsule 130. Each of the wires 144 is coupled to a corresponding terminal 146 of the motor 134. The wires 144 are arranged within the tether 132 and extend to the power supply 138.

In the illustrated non-limiting example, the power supply 138 is arranged externally from the capsule 130. The power supply 138 is in communication with the controller 126. In this non-limiting example, the controller 126 may be in wired or wireless communication with the power supply 138. In other non-limiting examples, the controller 126 may include an integrated power supply, in which case, the power supply 138 may not be required.

As will be described, in one non-limiting example, the wires 144 may be implemented in a control feedback strategy to control a rotational speed of the motor 134. In order to facilitate such a control feedback strategy, a circumferential position of the wires 144 within the capsule 130 may be fixed. In addition, to ensure proper optical coupling between the reflective surface 118 and the proximal end 114 of the optical waveguide 106, the motor 134 and the proximal end 114 of the optical waveguide 106 may be fixed within the capsule 130.

Figure 5:
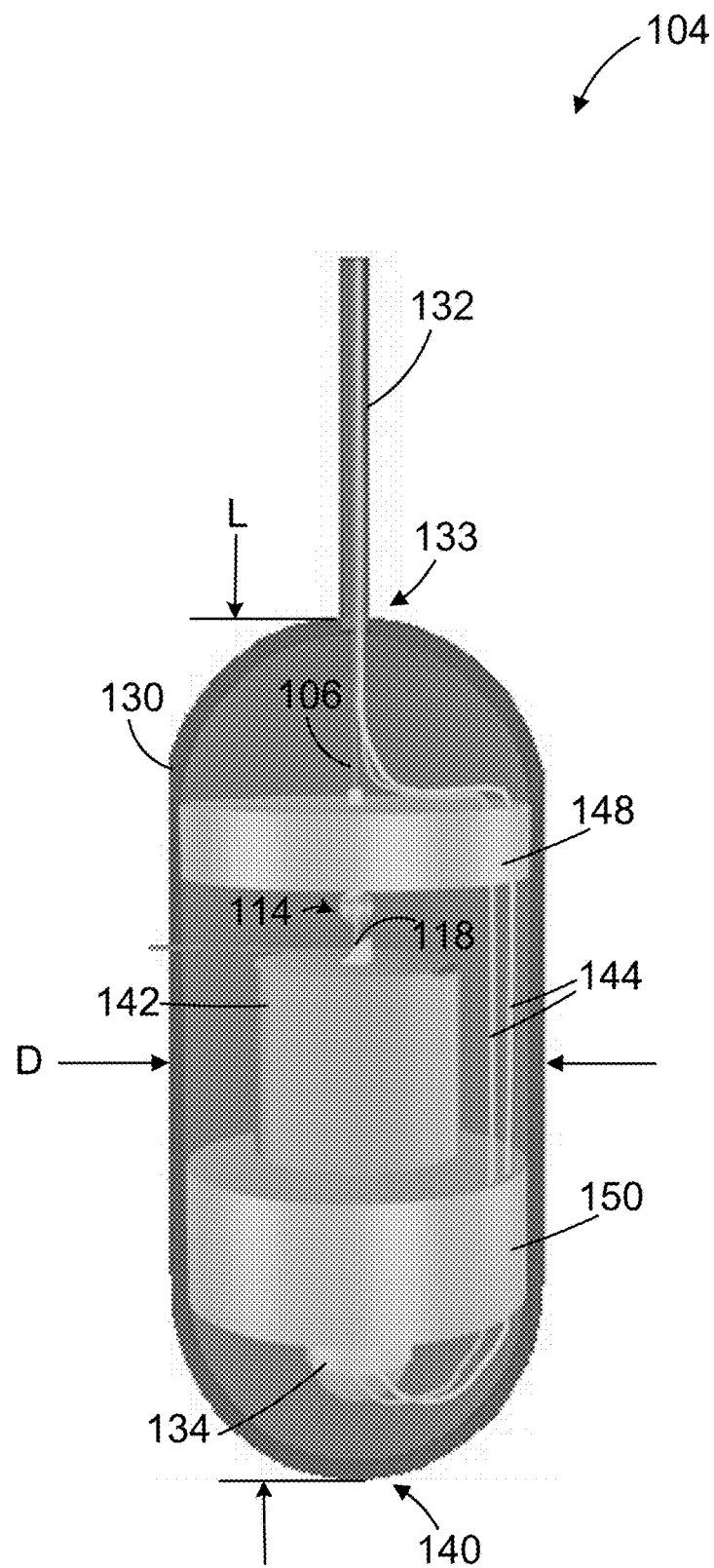
FIG. 5 is a schematic illustration of the wired tethered optical imaging probe of FIG. 4 including one or more supports arranged within a capsule.

FIG. 5 illustrates one non-limiting example of a mechanism for securing the proximal end 114 of the optical waveguide 106, the motor 134, and the wires 144 within the capsule 130. As shown in FIG. 5, the tethered optical imaging probe 104 may include a waveguide support 148 and a motor support 150 arranged within the capsule 130. The waveguide support 148 is secured within the capsule 130 and the proximal end 114 of the optical waveguide 106 extends therethrough to secure the proximal end 114 of the optical waveguide 106 in a fixed position adjacent to the reflective surface 118. The wires 144 extend through and are secured within a periphery of the waveguide support 148. The motor support 150 is secured within the capsule 130 and a portion of the motor 134 extends therethrough to secure the reflective surface 118 in a fixed position adjacent to the proximal end 114 of the optical waveguide 106. The wires 144 extend through and are secured within a periphery of the motor support 150. With the wires 144 extending through and secured within each of the waveguide support 148 and the motor support 150, a circumferential position of the wires 144 within the capsule 130 is fixed.

It should be appreciated that the illustrated waveguide support 148 and motor support 150 are not meant to be limiting in any way. That is, in other non-limiting examples, any securing mechanism (e.g., an adhesive) may be utilized to secure the proximal end 114 of the optical waveguide 106 and/or the motor 134 within the capsule 130.

Figure 6:
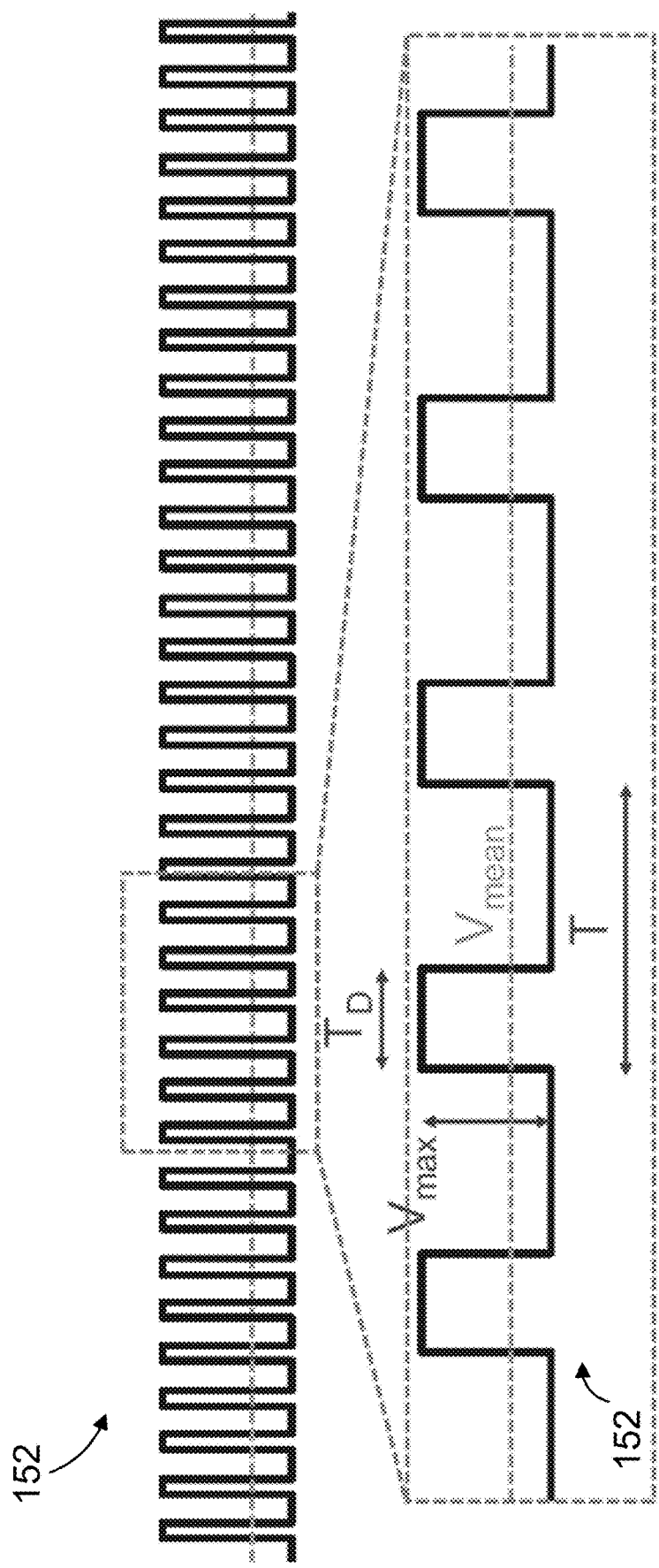
FIG. 6 illustrates a control signal applied to either the wireless tethered optical imaging probe of FIG. 3 or the wired optical imaging probe of FIG. 4 according to one aspect of the present disclosure.

As described above, a periodic signal may be supplied to the motor 134 by the controller 126. FIG. 6 illustrates one non-limiting example of a periodic control signal 152 configured to be supplied to the motor 134. As will be described, due to the inexpensive nature of the motor 134, supplying a constant voltage to the motor 134 is not sufficient to produce a controllable rotational speed suitable for high precision imaging. The use of a periodic control signal facilitates substantially increased accuracy and precision when controlling the rotational speed of the motor 134.

The illustrated periodic control signal 152 is in the form of a (positive) square wave comprising a plurality of pulses. Each of the plurality of pulses define a pulse width $T_D$ and a voltage magnitude $V_{max}$. In some non-limiting examples, the voltage magnitude $V_{max}$ may be between approximately 0 volts (V) and 10 V. A time between subsequent pulses, or period, T is defined to be larger than a natural time constant of the motor 134. In other words, a frequency (the inverse of the period T) defined by the periodic control signal 152 is chosen to be greater than a natural time constant of the motor 134. In one non-limiting example, the natural time constant of the motor 134 may be an inductive-resistive time constant. In some non-limiting examples, the frequency defined by the periodic control signal 152 may be greater than approximately 50 hertz (Hz) or greater than approximately 2 kilohertz (kHz). In certain cases, the frequency defined by the periodic control signal 152 may be between 50 Hz and 2 kHz. Although the periodic control signal 152 is generally described herein as being a square wave, this is merely an example, and any suitable waveform may be used to control the motor 134. For example, the periodic control signal 152 may be a triangle waveform, a sawtooth waveform, or a sinusoidal waveform. In some such examples, a DC offset may be added to the waveform and/or the waveform may (fully or partially, e.g., half-wave) rectified to prevent the motor 134 from reversing direction during a period of reversed polarity.

The periodic control signal 152 defines a mean voltage $V_{mean}$ that is defined by a ratio of the pulse width $T_D$ to the period T. The mean voltage $V_{mean}$ is proportional to a rotational speed of the motor 134. Thus, the pulse width $T_D$ and/or the frequency defined by the periodic control signal 152 may be modulated to control a rotational speed of the motor 134. In some cases, such as when the periodic control signal 152 is a square wave, $V_{mean}$ is proportional to the duty cycle of the periodic control signal 152. In some embodiments, where a waveform other than a square wave with is used (e.g., a triangle wave, a sawtooth wave, a sine wave), rather than controlling a duty cycle as described above in connection with a square wave, controlling a peak voltage level and/or DC offset to adjust $V_{mean}$. Additionally, although the motor 134 is generally described herein as being a DC motor, this is merely an example, and an AC motor may be used, in which case the speed of rotation may be based on the frequency of the periodic control signal.

To further facilitate accurate and precise control of the rotational speed of the motor 134, a feedback signal may be supplied to the controller 126 to enable the controller 126 to actively control the rotational speed of the motor 134 to a desired rotational speed. The feedback signal may be generated using software (e.g., via image processing) or using hardware (e.g., a signal generated within the capsule 130 and detected by the proximal end 114 of the optical waveguide 106).

Figure 7:
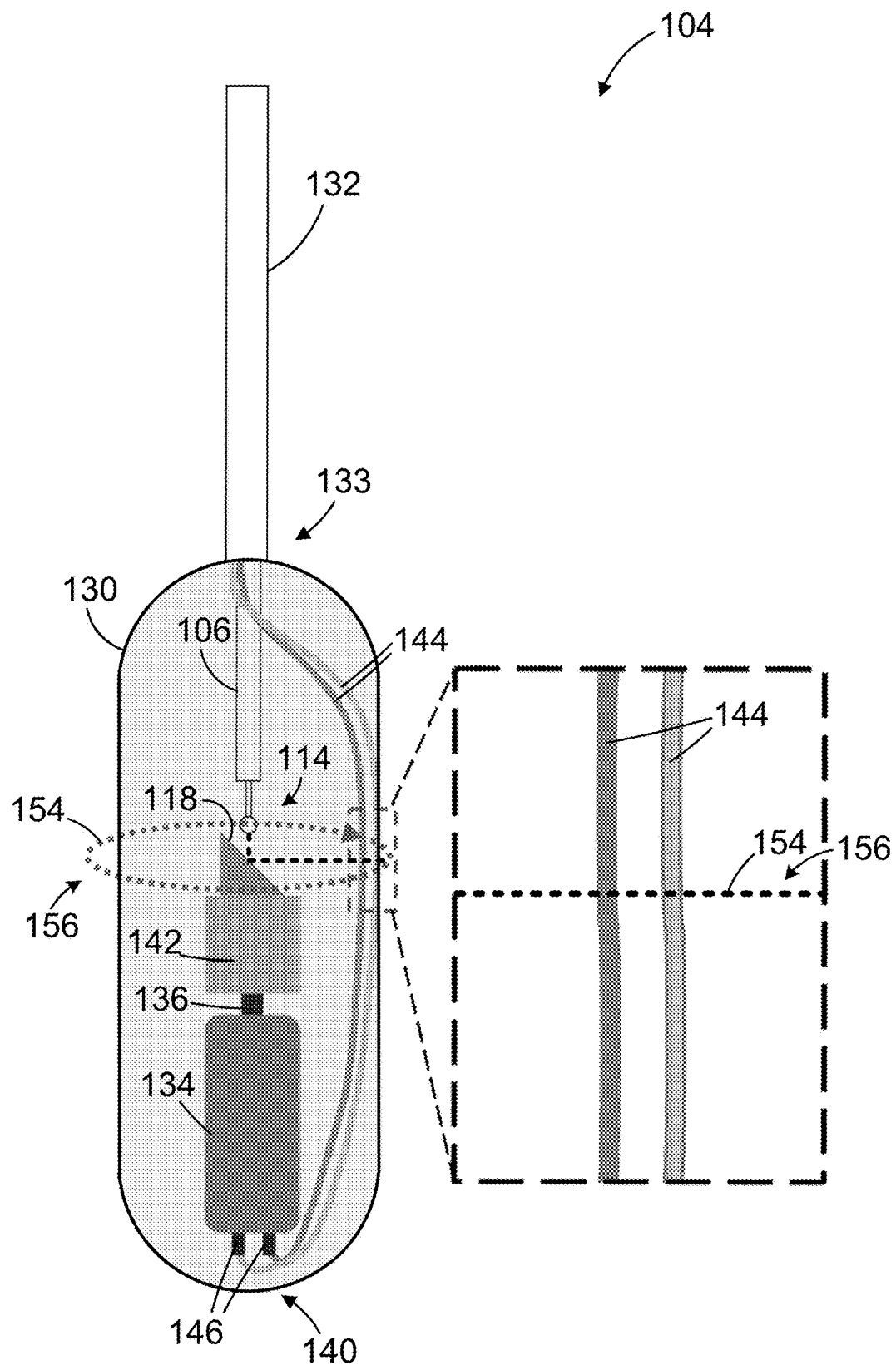
FIG. 7 is a schematic illustration of a motor control feedback strategy utilizing one or more wires according to one aspect of the present disclosure.

FIG. 7 illustrates one non-limiting configuration for generating a feedback signal. As shown in FIG. 7, during operation, the source light is emitted from the proximal end 114 of the optical waveguide 106 onto the reflective surface 118. The source light is then reflected, at an approximately 45° (degree) angle, radially outward through the capsule 130 and onto the sample 120. In certain cases, the angle of reflection can be adjusted slightly from the 45° angle in order to reduce and/or eliminate back reflections from the capsule 130. In certain cases, the angle of reflection can be 41° or 49°, though other angles of reflection are contemplated. As the motor 134 rotates the reflective surface 118, the source light is rotated circumferentially around the capsule to form a circumferential optical path 154 traversed by the source light. The motor 134, the reflective surface 118, and the proximal end 114 of the optical waveguide 106 are positioned to provide a circumferential field of view 156 that encompasses a portion of the capsule 130 for detecting light reflected from the sample 120. The circumferential field of view 156 generally overlaps with the circumferential optical path 154 traversed by the source light. In this way, the reflective surface 118 is arranged to reflect source light from the proximal end 114 of the optical waveguide 106 onto the sample 120 and reflect light from the sample 120 back to the proximal end 114 of the optical waveguide 106.

In some non-limiting examples, a detection object may be arranged in the circumferential optical path and/or the circumferential field of view to facilitate the generation of the feedback signal. A feedback signal generated by or from the detection object may be detected as the reflective surface 118 is rotatably positioned by the motor 134 to align with the detection object to direct the feedback signal from the detection object to the proximal end 114 of the optical waveguide 106 for transmission to the distal end 112 of the optical waveguide 106.

In the non-limiting example of FIG. 7, the detection object may be in the form of the wires 144 may be used to generate the feedback signal supplied to the controller 126. The wires 144 possess various properties that are useful in generating the feedback signal. For example, the wires 144 may cast a shadow radially in an image acquired by the optical detector 122, when the reflective surface 118 is rotatably positioned by the motor 134 to align with the wires 144. The capsule 130 may be visible in the image acquired by the optical detector 122, except where the shadow is cast by the wires 144. Since the wires 144 define a known thickness and are circumferentially fixed within the capsule 130, a change in the radial position of the shadow cast by the wires 144 in images acquired by the optical detector 122 may be utilized to generate a feedback control signal. That is, the signal from the wires 144 must occur once per rotation of the motor 134 and periodically, if the motor 134 rotates at a substantially constant speed. Any deviation of the periodicity in the signal from the wires 144 indicates a change in the rotational speed of the motor 134. This change in periodicity may be utilized to estimate a change in the rotational speed of the motor 134 and provide a feedback signal to the controller 126.

In some non-limiting examples, an image processing algorithm may be implemented to detect changes in the radial position of the shadow cast by the wires 144 in the images acquired by the optical detector 122. In one non-limiting example, an image processing algorithm may involve determining averages along the radial direction in the images acquired by the optical detector 122 where the wires 144 are expected to be present and regions where the capsule 130 is expected to be present. A ratio or difference of the two radial region averages may be one possible metric utilized to generate a feedback control signal. It should be appreciated that the techniques described herein utilizing the wires 144 to generate a feedback signal may only require at least one of the wires 144 to facilitate generating the feedback signal.

In some non-limiting examples, the wires 144 may be coated with a material (e.g., a paint, nail polish) to enhance back-scattering of reflected source light from the wires 144 to the reflective surface 118. That is, the wires 144 may be at least partially reflective to the source light. The back-scattered, reflected source light, or signal, from the wires 144 may be identified via image processing, as described above, or via hardware detection (e.g., optical filtering and detection by reflection off of the reflective surface 118 into the proximal end 114 of the optical waveguide 106). Again, any deviation in the periodicity in the signal from the wires 144 indicates a change in the rotational speed of the motor 134 and may be utilized to provide a feedback signal to the controller 126.

In some non-limiting examples, the wires 144 may be coated with a phosphorescent coating, a fluorescent coating, a quantum dot coating, or a combination thereof. In this non-limiting example, the coating applied to the wires 144 may be configured to absorb a portion of the source light reflected from reflective surface 118 and subsequently emit signal light at a wavelength different than the source light back to the reflective surface 118 and into the proximal end 114 of the optical waveguide 106. The signal light emitted by the wires 144 may be optically filtered (e.g., via a wavelength division multiplexer, a dichroic mirror, etc.) and utilized to provide a feedback control signal to the controller 126. The signal light emitted from the wires 144 may be detected as the reflective surface 118 is rotatably positioned by the motor 134 to direct the emitted signal light from the light emitting material to the proximal end 114 of the optical waveguide 106. Again, any deviation in the periodicity in the signal light emitted from the wires 144 indicates a change in the rotational speed of the motor 134 and may be utilized to provide a feedback signal to the controller 126.

Figure 8:
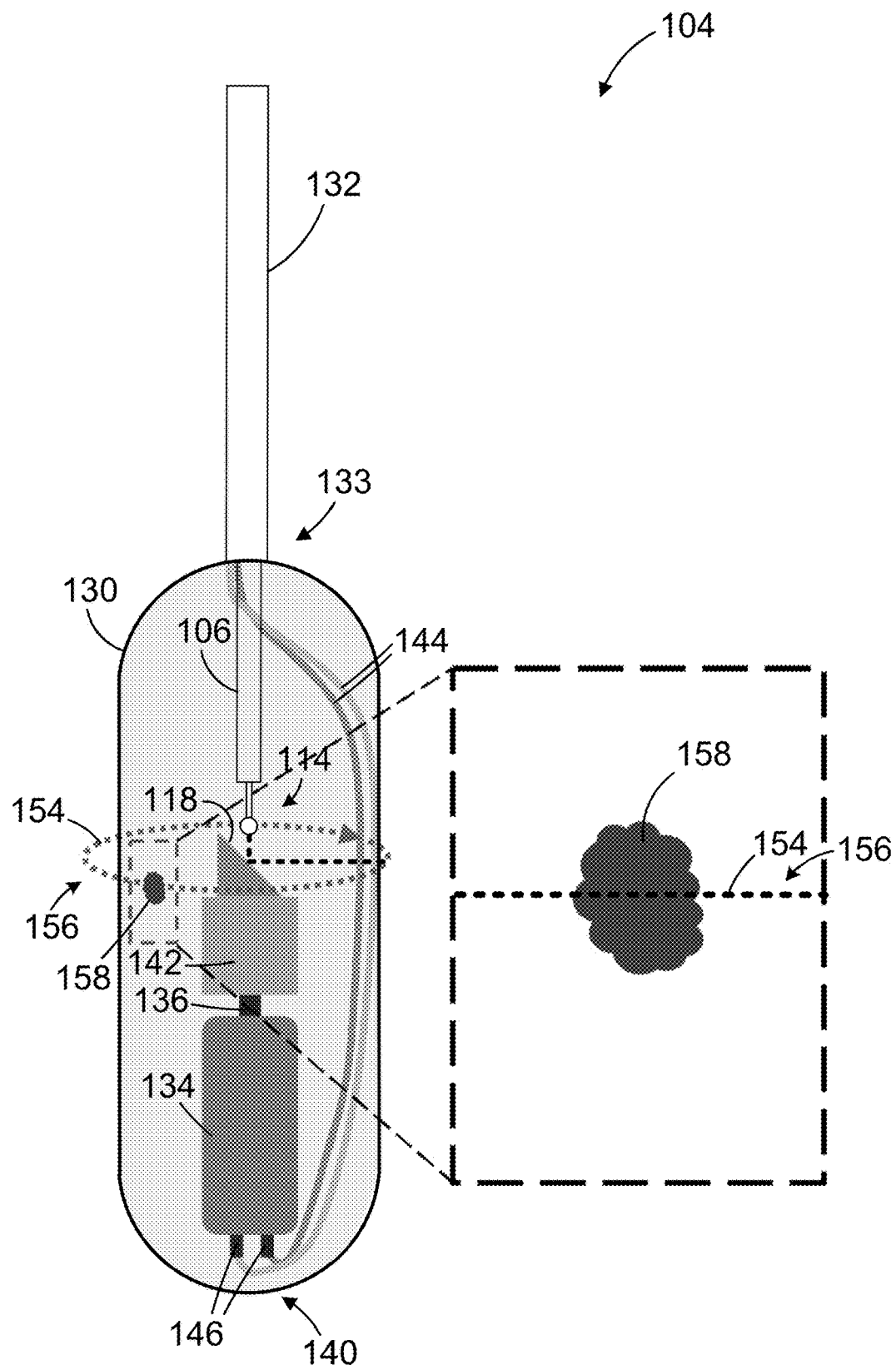
FIG. 8 is a schematic illustration of a motor control feedback strategy utilizing a light emitting material according to one aspect of the present disclosure.

FIG. 8 illustrates another non-limiting configuration for generating a feedback signal. As shown in FIG. 8, the capsule 130 may include a detection object 158 arranged on the capsule 130 and within a portion of the circumferential field of view and/or a portion of the circumferential optical path. In one non-limiting example, the detection object 158 may be in the form of a light emitting material. The light emitting material may be a phosphorescent material, a fluorescent material, a quantum dot material, or a combination thereof. The light emitting material may be configured to absorb a portion of the source light reflected from reflective surface 118 and subsequently emit signal light at a wavelength different than the source light back to the reflective surface 118 and into the proximal end 114 of the optical waveguide 106. The signal light emitted from the light emitting material may be optically filtered (e.g., via a wavelength division multiplexer, a dichroic mirror, etc.) and utilized to provide a feedback control signal to the controller 126. The signal light emitted from the light emitting material may be detected as the reflective surface 118 is rotatably positioned by the motor 134 to direct the emitted signal light from the light emitting material to the proximal end 114 of the optical waveguide 106. Again, any deviation in the periodicity in the signal light emitted from the light emitting material indicates a change in the rotational speed of the motor 134 and may be utilized to provide a feedback signal to the controller 126.

In other non-limiting examples, the detection object 158 may be in the form of a light reflecting material. It should be appreciated that although the non-limiting configuration of FIG. 8 illustrates the wires 144 within the tethered optical imaging probe 104, the feedback signal is generated via the detection object 158. Therefore, in the non-limiting example of FIG. 8, the wires 144 may not be required, and the tethered optical imaging probe 104 may alternatively be in the wireless configuration of FIG. 3.

Figure 9:
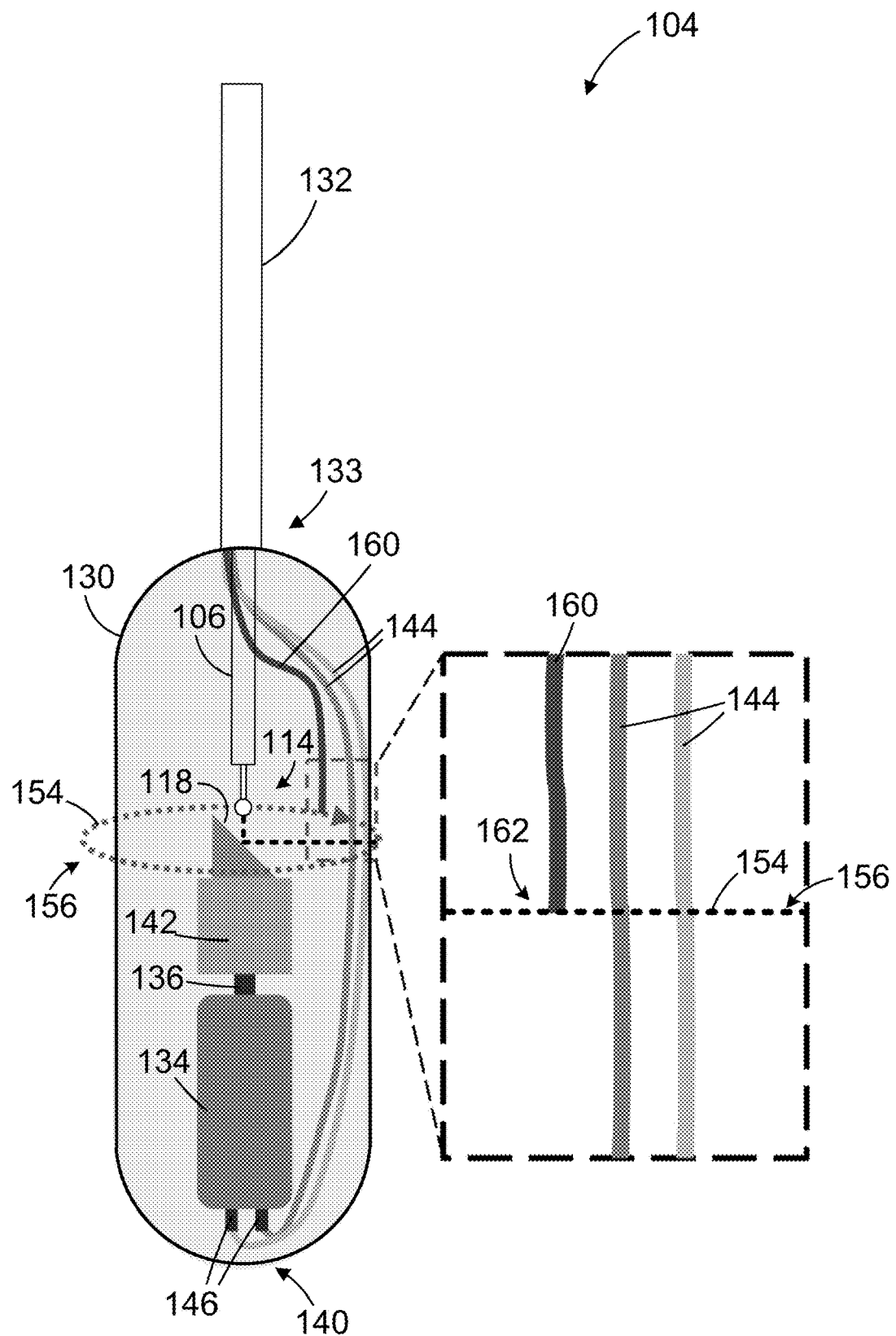
FIG. 9 is a schematic illustration of a motor control feedback strategy utilizing a secondary optical waveguide according to one aspect of the present disclosure.

FIG. 9 illustrates another non-limiting configuration for generating a feedback signal. As shown in FIG. 9, the tethered optical imaging probe 104 may include a secondary optical waveguide 160 inserted into the first end 133 of the capsule 130. The detection object may be in the form of the secondary optical waveguide 160. The secondary optical waveguide 160 is arranged receive a portion of the source light reflected from the reflective surface 118 as the reflective surface 118 is rotated by the motor 134. That is, the secondary optical waveguide 160 includes a secondary proximal end 162 arranged at least partially within the circumferential optical path. The feedback signal may be generated as the reflective surface 118 is rotatably positioned by the motor 134 to direct source light into the secondary proximal end 162 of the secondary optical waveguide 160. The feedback signal detected by the secondary optical waveguide 160 may be transmitted to a secondary distal end 164 thereof. Again, any deviation in the periodicity in the feedback signal detected by the secondary optical waveguide 160 indicates a change in the rotational speed of the motor 134 may be utilized to provide a feedback signal to the controller 126.

It should be appreciated that although the non-limiting configuration of FIG. 9 illustrates the wires 144 within the tethered optical imaging probe 104, the feedback signal is generated via the secondary optical waveguide 160. Therefore, in the non-limiting example of FIG. 9, the wires 144 may not be required, and the tethered optical imaging probe 104 may alternatively be in the wireless configuration of FIG. 3.

EXAMPLES

The following examples set forth, in detail, ways in which the optical system 100 and/or the tethered optical imaging probe 104 may be used or implemented, and will enable one of skill in the art to more readily understand the principles thereof. The following examples are presented by way of illustration and are not meant to be limiting in any way.

Motor Characterization

Exemplary operational parameters for the motor used in the Examples can be as follows: a maximum voltage applied to the motor ($V_{max}$) can be 3V; a period of pulsed voltage applied to the motor (T) can be 1 millisecond (ms); a pulse duration of pulsed voltage applied to the motor ($T_d$) can be 166 microseconds (µs); a mean voltage applied to the motor ($V_{mean}$) can be 0.5V; and a damping weight can be 1.7 g. An exemplary motor used in the Examples is motor 103-100 from Precision Microdrives (available commercially from Precision Microdrives, London, United Kingdom).

Figure 10:
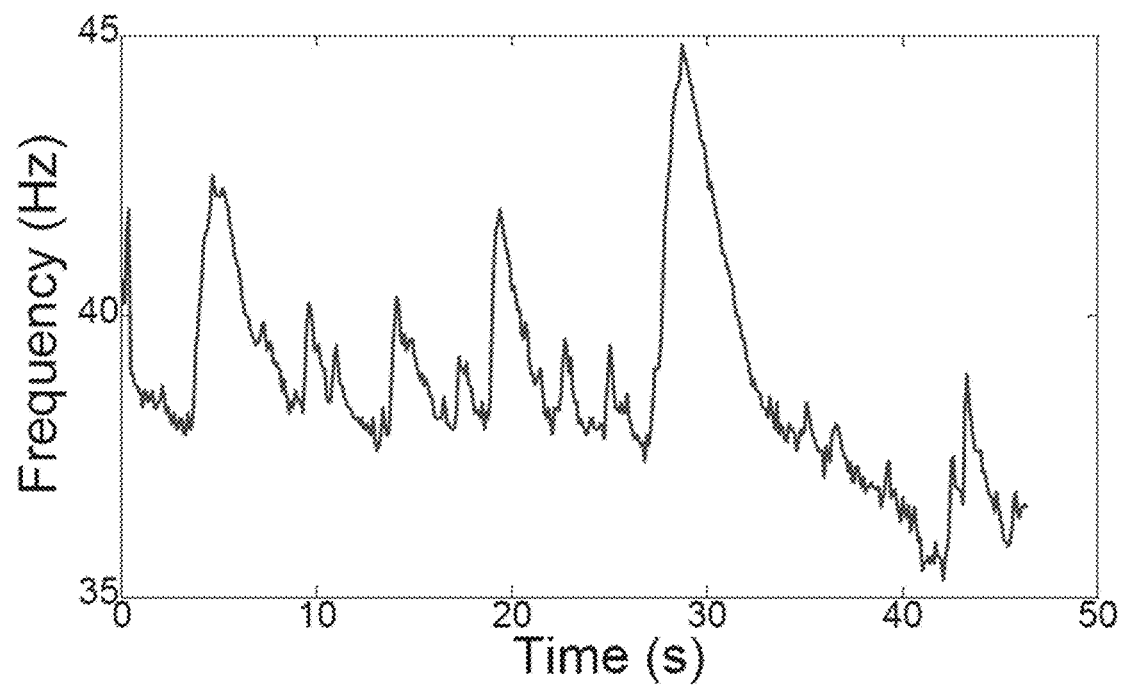
FIG. 10 is graph illustrating a motor speed as a function of time with a constant voltage applied to the motor.

A low-cost, cell phone motor was tested to determine a speed profile of the motor as a function of time with a constant DC voltage applied thereto. As shown in FIG. 10, the motor speed (represented in frequency of rotation) substantially varies as a function of time with the constant DC voltage applied to the motor. Thus, supplying a constant DC voltage to the motor 134 is not sufficient to facilitate high precision imaging, where the rotational speed of the motor must be accurately controlled.

Figure 11:
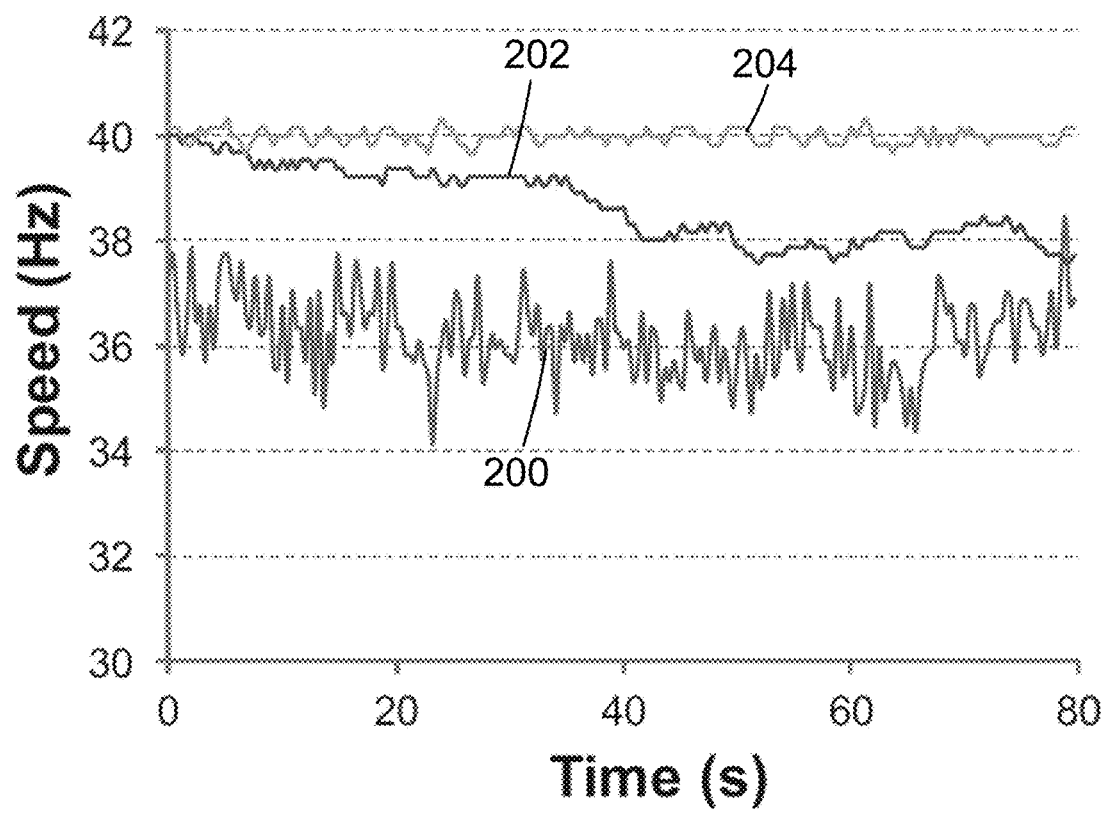
FIG. 11 is a graph illustrating a motor speed as a function of time with a constant voltage applied to the motor, a periodic control signal applied to the motor, and a periodic control signal applied to the motor with a feedback signal.

Next, a periodic signal was applied to the motor in an attempt to improve the accuracy and precision in the speed profile generated during operation of the motor. In addition, a feedback signal, which indicated a change in a rotational speed of the motor, was supplied to a controller to modulate the periodic signal applied to the motor. The motor was attempted to be controlled at a constant speed of 40 Hz. FIG. 11 illustrates the results of the test with line 200 representing a constant DC voltage applied to the motor with no feedback signal, line 202 representing a periodic control signal applied to the motor with no feedback signal, and line 204 representing a periodic control signal applied to the motor with a feedback signal. As shown in FIG. 11, applying a constant DC voltage to the motor with no feedback signal (line 200) resulted in an erratic speed profile that was offset from 40 Hz (i.e., averaged approximately 37 Hz). Applying a periodic control signal to the motor with no feedback loop (line 202) improved the precision and accuracy in the speed profile as a function of time. Lastly, when a periodic signal was applied to the motor with a feedback loop (line 204), the speed profile drastically improved in accuracy and precision, when compared to lines 200 and 202.

Figure 12:
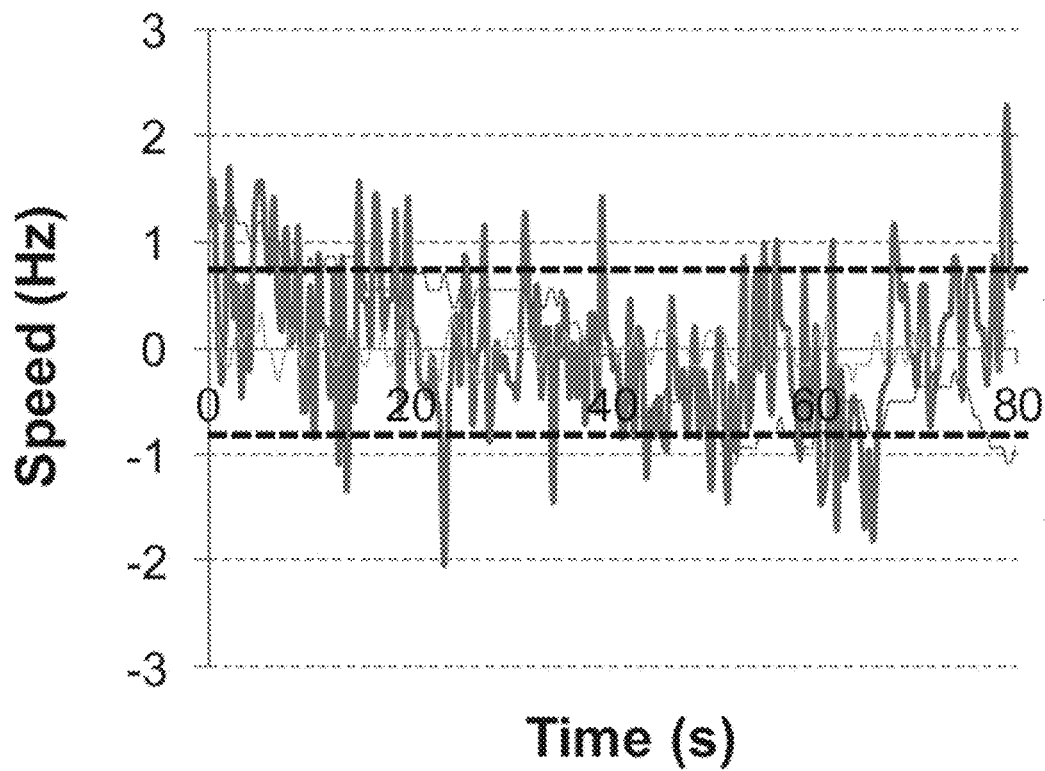
FIG. 12 is a graph illustrating a deviation profile as a function of time of the motor speed of FIG. 11 with a constant voltage applied to the motor.
Figure 13:
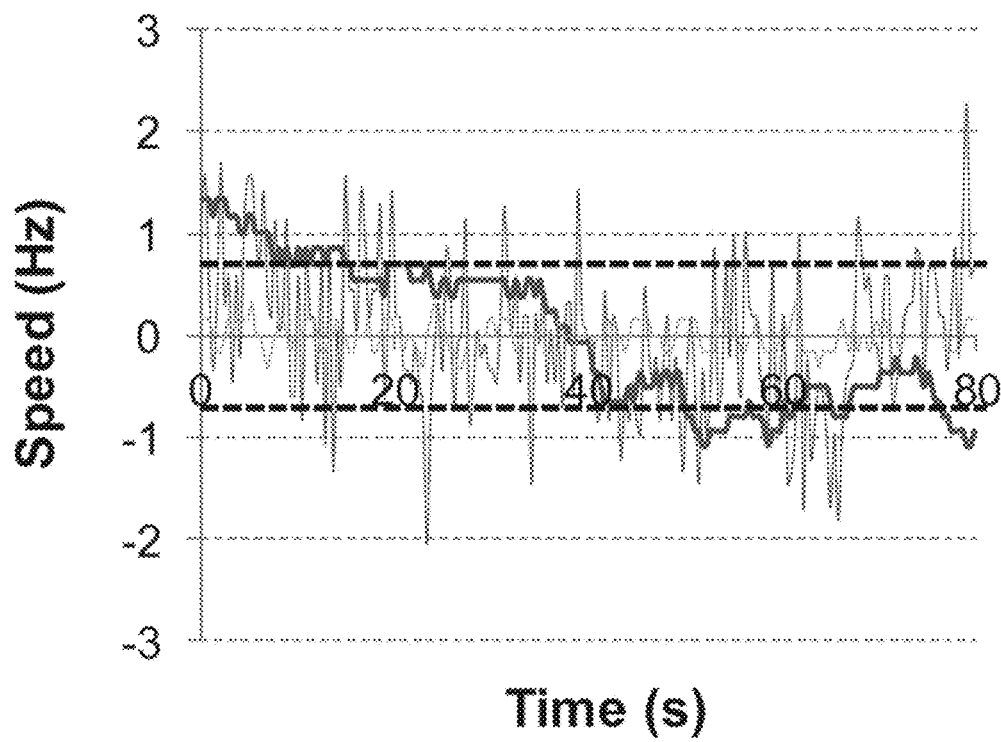
FIG. 13 is a graph illustrating a deviation profile as a function of time of the motor speed of FIG. 11 with a periodic voltage applied to the motor.
Figure 14:
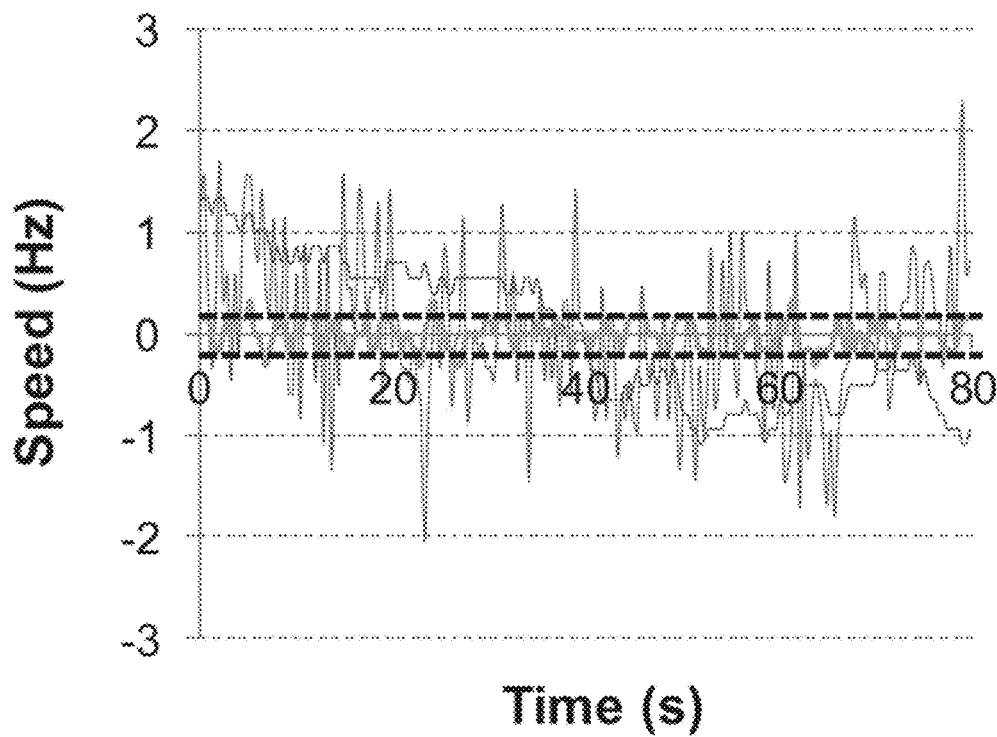
FIG. 14 is a graph illustrating a deviation profile as a function of time of the motor speed of FIG. 11 with a periodic voltage applied to the motor with a feedback signal.

To supplement the data shown in FIG. 11, FIGS. 12, 13, and 14 illustrate a deviation profile of each of lines 200, 202, and 204, respectively. The deviation profiles were calculated by subtracting the lines 200, 202, and 204 from their means. The standard deviations defined by the derivation profiles in FIGS. 12, 13, and 14 are 0.76, 0.71, and 0.17, respectively. Thus, the application of a periodic control signal to the motor and the feedback loop drastically improve the precision in the output speed profile of the motor.

Figure 15:
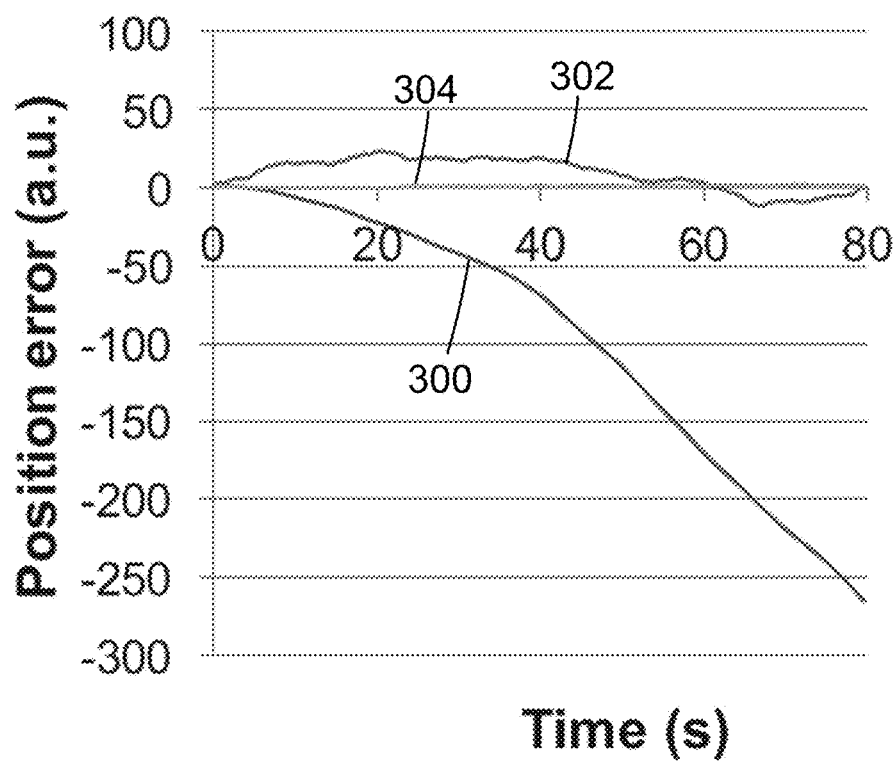
FIG. 15 is a graph illustrating a position error as a function of time for a motor with a constant voltage applied to the motor, a periodic control signal applied to the motor, and a periodic control signal applied to the motor with a feedback signal.

FIG. 15 illustrates a position error of the motor as a function of time for the motor with line 300 representing a constant DC voltage applied to the motor with no feedback signal, line 302 representing a periodic control signal applied to the motor with no feedback signal, and line 304 representing a periodic control signal applied to the motor with a feedback signal. Position of the motor is defined as the direction in which a laser beam is directed (relative to an absolute position, like the position of wires, for example). Position error is the difference between the actual motor position and the expected motor position if the motor is spinning under "ideal" conditions or constant speed. As shown in FIG. 15, the position error is negligible when the periodic control signal is applied to the motor with a feedback signal.

Figure 16:
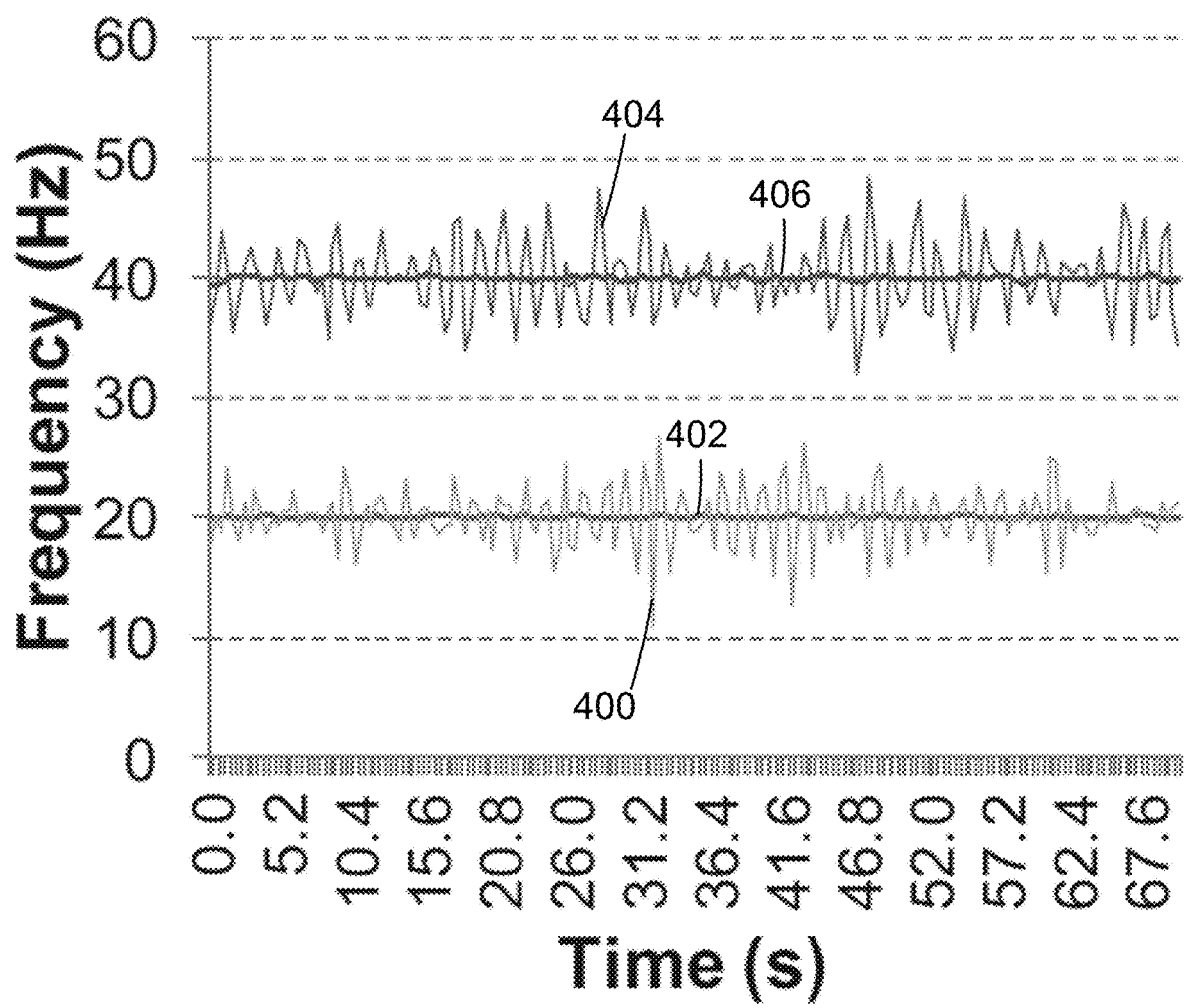
FIG. 16 is a graph illustrating motor speed as a function of time at a motor speed of 20 Hz and 40 Hz with and without a damping weight coupled to the motor.

FIG. 16 illustrates the result of implementing the damping weight 142 on the feedback loop performance. The motor was controlled to 20 Hz for lines 400 and 402 with line 402 including the damping weight 142 and line 400 not including the damping weight 142. The motor was controlled to 40 Hz for lines 404 and 406 with lines 406 including the damping weight 142 and line 404 not including the damping weight 142. As shown in FIG. 16, the precision of the speed profile substantially improved at both 20 Hz and 40 Hz when the damping weight 142 was attached to the motor (i.e., lines 400, 402, 404, and 406 define standard deviations of 2.5, 0.07, 3.06, and 0.166, respectively).

In certain embodiments, visualization of the villi by tethered capsule OCT endomicroscopy may be adapted and optimized for comprehensive imaging of the human duodenum, for example to diagnose conditions such as celiac disease. Celiac disease (CD) affects around 1% of the global population and can cause serious long-term symptoms including malnutrition, fatigue, and diarrhea, amongst others. Celiac disease is an inflammatory autoimmune condition of the small intestine, triggered by gluten in genetically-susceptible individuals. Classic symptoms include gastrointestinal problems such as chronic diarrhea, abdominal distention, malabsorption etc., however, non-classic symptoms are the most common, especially in people older than two years. Celiac disease is estimated to affect 1 in 100 people worldwide and 1 in 133 Americans. Two and one-half million Americans are undiagnosed and are at risk for long-term health complications.

Despite the potential health implications, CD is often left undiagnosed. Currently, a tissue diagnosis of CD is made by random endoscopic biopsy of the duodenum to confirm the existence of microscopic morphologic alterations in the intestinal mucosa. However, duodenal endoscopic biopsy is problematic because the morphological changes can be focal and endoscopic biopsy is plagued by sampling error. Additionally, tissue artifacts can be a problem because cuts in the transverse plane can make duodenal villi appear artifactually shortened and can bias the assessment of intraepithelial inflammation. Moreover, endoscopic biopsy is costly and poorly tolerated, as the patient needs to be sedated to perform the procedure.

Tethered capsule OCT endomicroscopy (TCE) has been developed to overcome diagnostic limitations of endoscopy. TCE involves swallowing an optomechanically-engineered pill that generates 3D images of the GI tract as it traverses the lumen of the organ via peristalsis, assisted by gravity. Although TCE imaging of duodenal villi has been demonstrated in some patients, current TCE device designs are not optimal for diagnosing CD as the villi may be compressed when in contact with the smooth wall of the capsule. Thus, disclosed herein are embodiments of a capsule in which the capsule outer surface is structured to improve the visualization of the villi height and crypt depth. Preliminary results in humans suggest that the modified TCE capsule enables better visualization of villous architecture, making it possible to comprehensively scan the entire duodenum to obtain a more accurate tissue diagnosis of CD. Note that, in addition to CD, other diseases and conditions may also induce villi morphological changes, such as drug-induced enteroptathy (e.g., as a side-effect of Benicar), Common Variable Immunodeficiency, Small Intestine Bacterial Overgrowth, Crohn's Disease, Intestinal Lymphoma, Autoimmune enteropathy, and Environmental Enteric Dysfunction, and capsule embodiments described herein may also enable more accurate diagnosis of such diseases and/or conditions.

Figure 17:
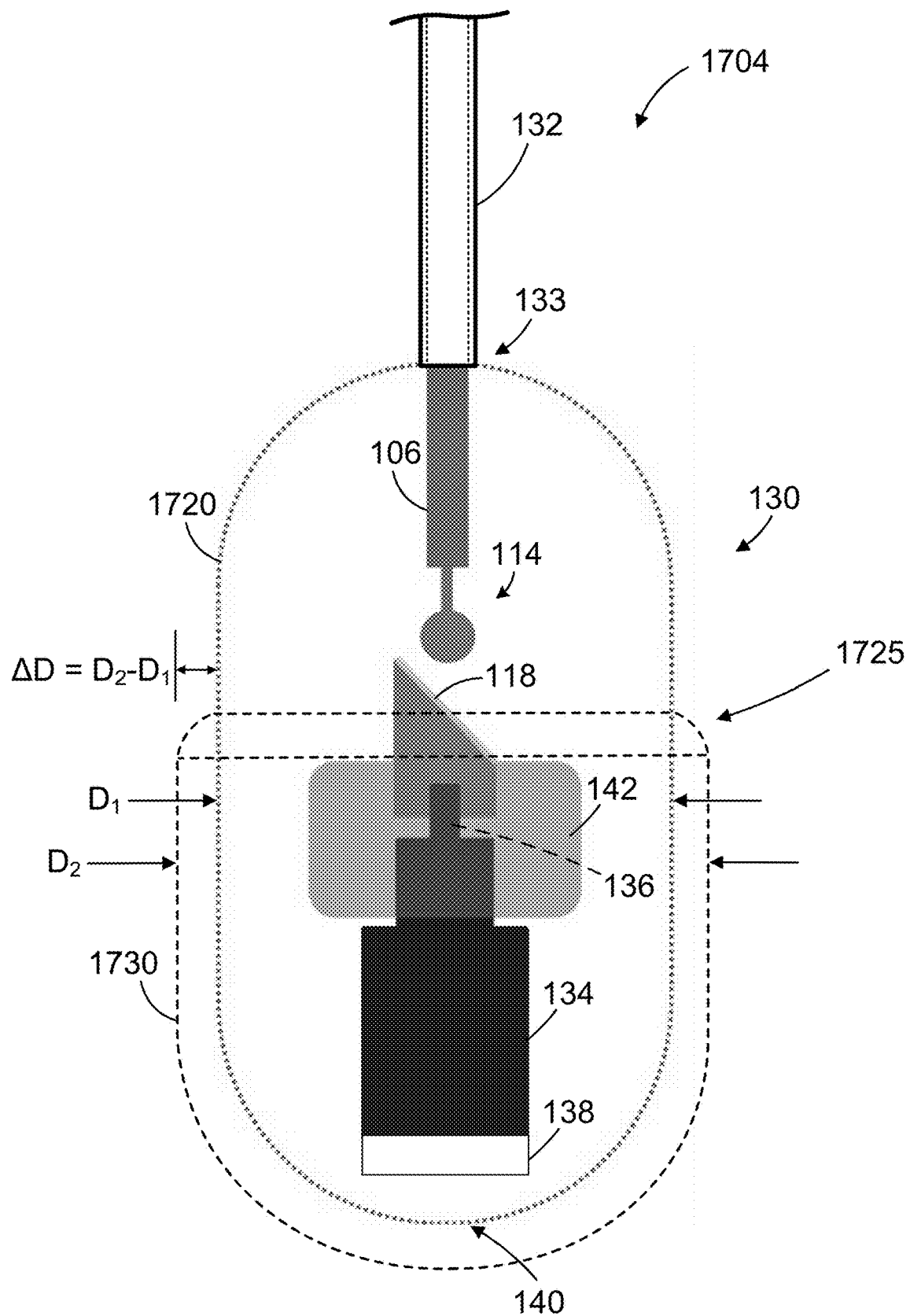
FIG. 17 is a schematic illustration of a tethered optical imaging probe according to one aspect of the present disclosure.
Figure 18:
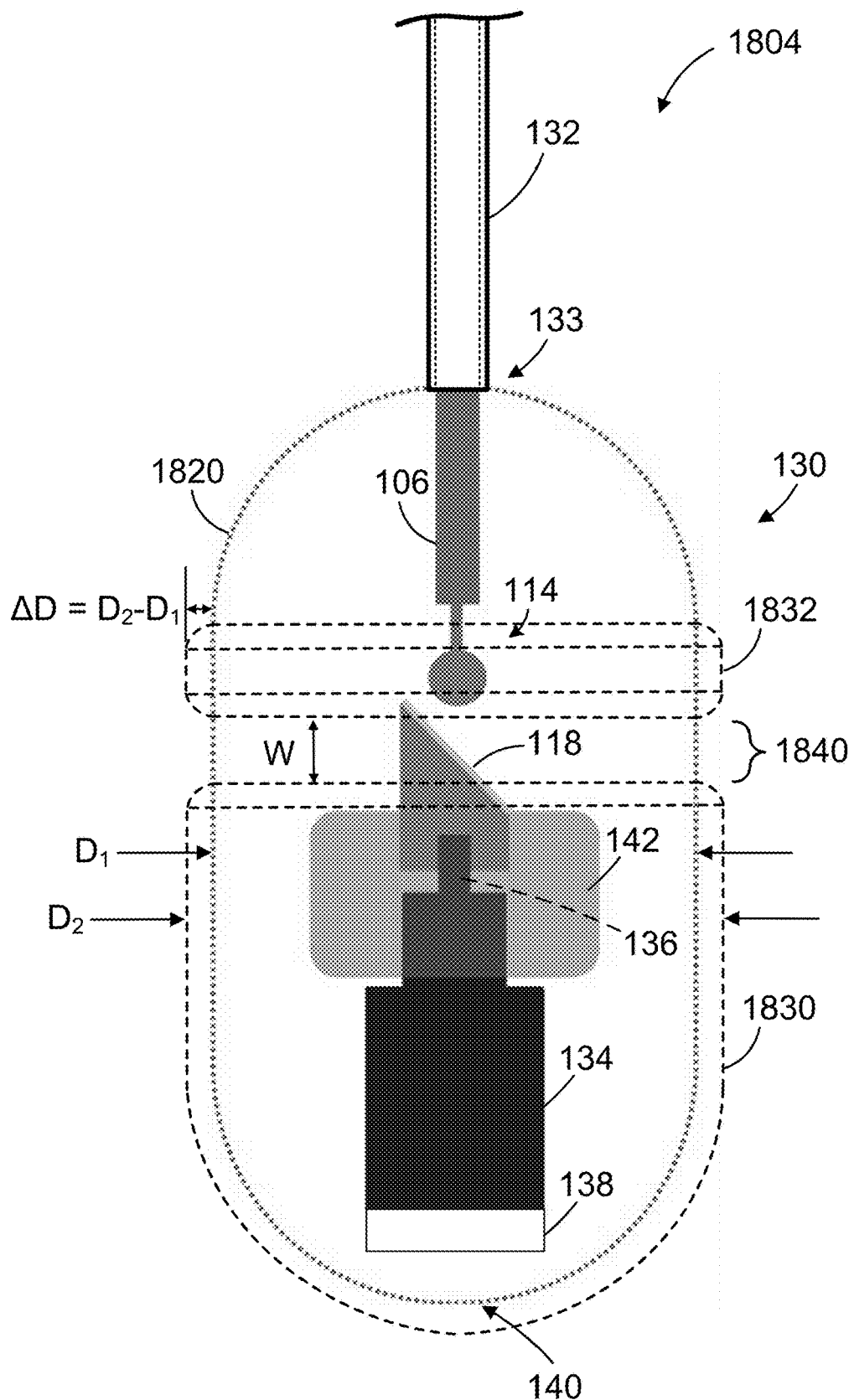
FIG. 18 is a schematic illustration of a tethered optical imaging probe according to one aspect of the present disclosure.

In some embodiments, the capsule 130 of the tethered optical imaging probe 104 may have one or portions with different diameters to facilitate CD diagnosis (FIGS. 17, 18). Thus, in one particular embodiment of a tethered optical imaging probe 1704, the body of the capsule 130 may be generally cylindrical with a cross-section of the capsule 130 having a first portion 1720 having a first diameter $D_1$ and a second portion 1730 having a second diameter $D_2$ larger than the first diameter, and a difference between the diameters of: $\Delta D = D_2 - D_1$ (FIG. 17). In some embodiments the larger diameter $D_2$ of the second portion 1730 may extend around an end of the capsule 130 such as the distal end (FIG. 17) or the proximal end, where either or both ends of the capsule 130 may be hemispherical in shape. Between the first portion 1720 and the second portion 1730 is a transition 1725 with a diameter that varies between the first diameter $D_1$ and the second diameter $D_2$, for example in a gradual beveled shape or a rounded shape. As a result of the difference $\Delta D$ in diameters between the first portion 1720 and the second portion 1730, tissue (such as duodenal villi) that is adjacent to the first portion 1720 in the vicinity of the transition 1725 is not compressed by the body of the capsule 130. In general, a field of view of the tethered optical imaging probe 1704 encompasses at least a section of the first portion 1720 that is adjacent to the transition 1725. That is, the transition 1725 between the first portion 1720 and the second portion 1730 is situated relative to the reflective surface 118 so that light reflected laterally/radially from the reflective surface 118 is directed toward a section of the first portion 1720 of the capsule 130 that is near the transition 1725, allowing tissue in this region to be imaged in a more natural, non-compressed state. In certain embodiments the difference in diameters $\Delta D$ may be between 0.5 mm and 2.0 mm, and in one particular embodiment the difference $\Delta D$ may be 1.0 mm.

In another embodiment of a tethered optical imaging probe 1804, the capsule 130 has a first portion 1820 having a first diameter $D_1$ and a second portion 1830 having a second diameter $D_2$ larger than the first diameter, and a difference between the diameters of: $\Delta D = D_2 - D_1$ (FIG. 18). The capsule 130 may further include a third portion 1832 having a diameter than is larger than the diameter $D_1$ of the first portion; for example the diameter of the third portion may be equal to the diameter of the second portion, namely $D_2$. However, in various embodiments the third portion may have other diameters that are larger than the diameter of the first portion, diameters that may be larger or smaller than $D_2$. The third portion 1832 may cover only a band around the circumference of the cylindrical body of the capsule 130 and may include transition portions on each side of the band that transition from the diameter of the first portion 1820 to the diameter of the third portion 1830, where the transitions may have different shapes such as beveled or rounded.

Figure 1:
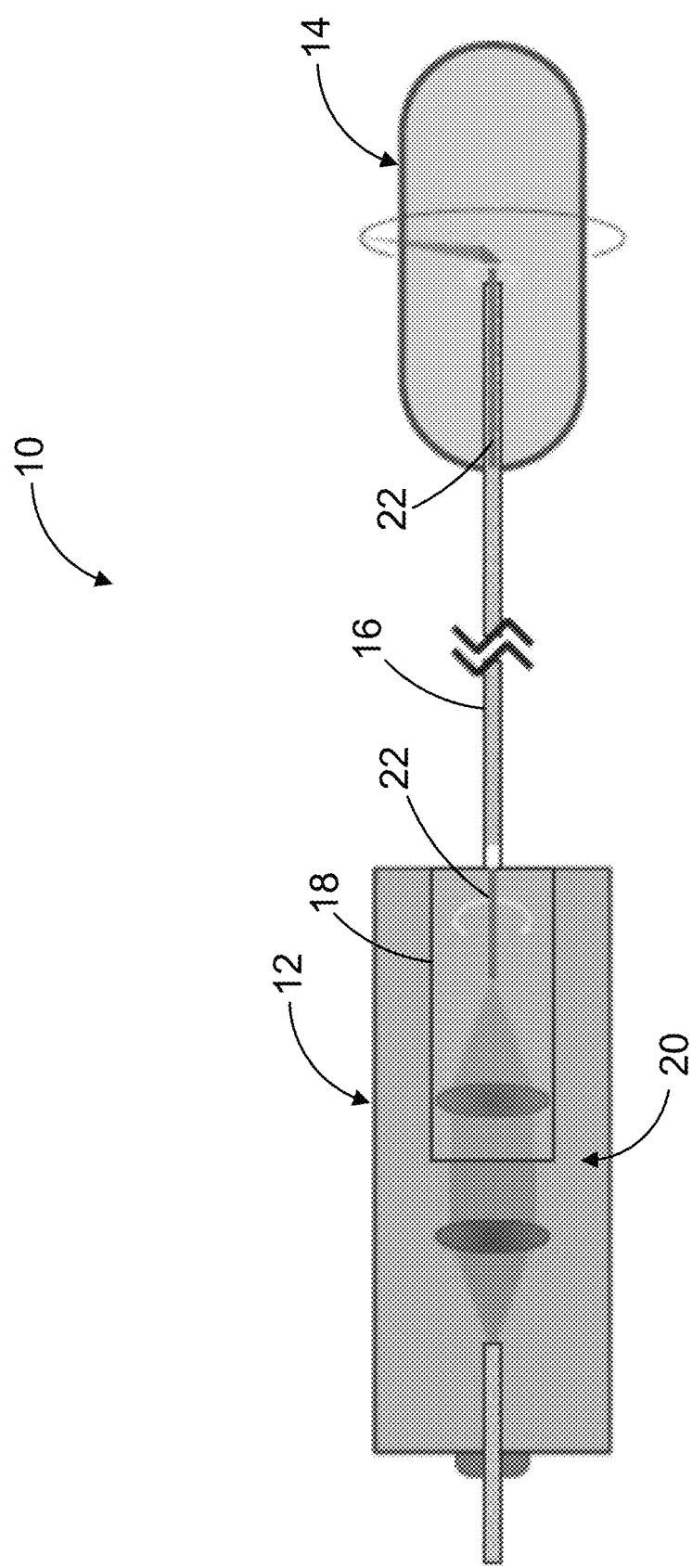
FIG. 1 is a schematic illustration of a tethered optical imaging device according to the prior art.

The third portion 1832 is generally situated relative to the reflective surface 118 and relative to the second portion 1830 such that there is a region of smaller diameter $D_1$ between the larger-diameter second portion 1830 and third portion 1832, the region being aligned with the reflective surface 118 such that light reflected from the reflective surface 118 exits the capsule 130 in the smaller diameter zone termed a notch 1840 (FIG. 18). That is, the third portion 1832 is generally situated relative to the reflective surface 118 and relative to the second portion 1830 such that a field of view of the tethered optical imaging probe 1804 encompasses at least a section of the notch 1840. The notch 1840 may have a width W which is defined by the spacing between the second portion 1830 and the third portion 1832 (as well as any transition regions associated with the portions). Due to compression being reduced or eliminated in this region, tissue that is located adjacent the notch 1840 may be imaged in a more natural, non-compressed state, which may facilitate a CD diagnosis. In various embodiments the width W of the notch 1840 may be between 1.0 mm and 4.0 mm, and in one particular embodiment the width W may be 2.0 mm. In certain embodiments the depth or thickness of the notch 1840 (determined by the difference in diameters $\Delta D$) may be between 0.25 mm and 2.0 mm, and in one particular embodiment the depth of the notch 1840 may be 0.5 mm. Note that, although the capsules described above in connection with FIGS. 17 and 18 are generally described as being used to implement a tethered imaging probe with a motor (e.g., motor 134) rotating optics within the capsule, this is merely an example, and the features described in connection with FIGS. 17 and 18 can be used with tethered imaging probes that include rotating optics within the tether (e.g., as described above in connection with FIG. 1).

Figure 19:
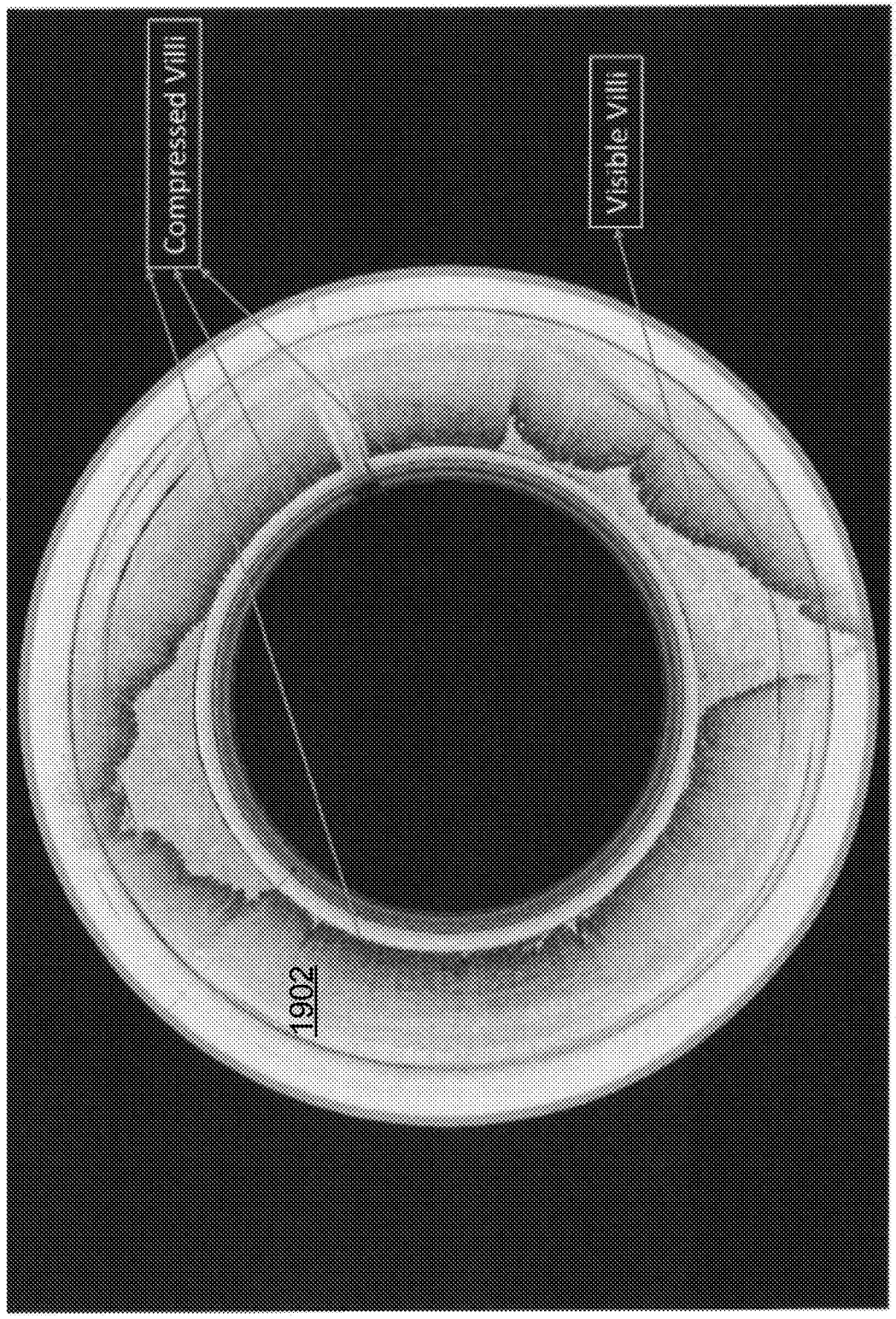
FIG. 19 is an image of a duodenum imaged using a tethered optical imaging probe with a capsule having a single outer diameter.
Figure 20:
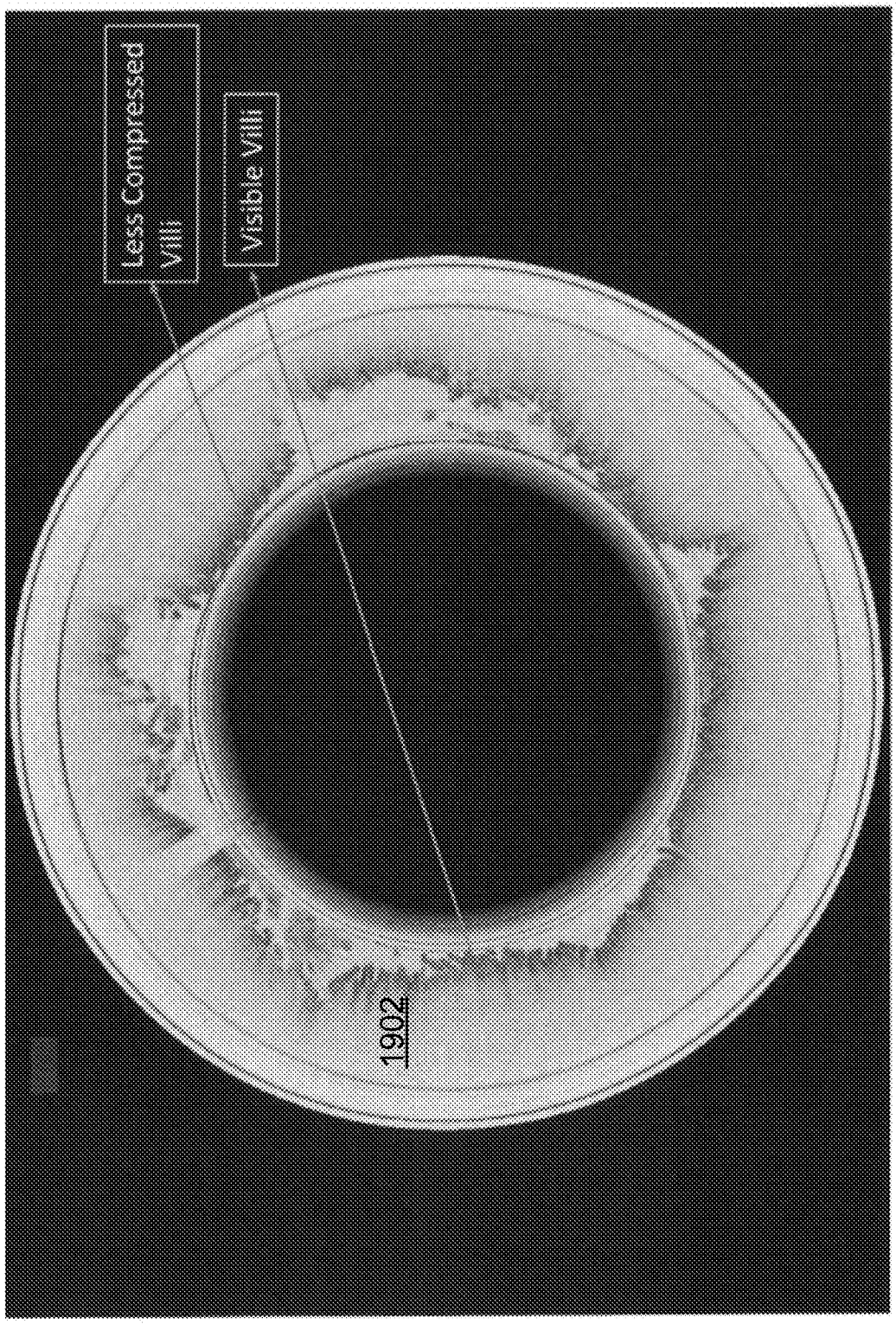
FIG. 20 is an image of a duodenum imaged using a tethered optical imaging probe with a capsule having a notch such as that shown in FIG. 18.

FIG. 19 shows data that was collected from a duodenum region of a patient using a tethered OCT capsule system with a conventional pill-shaped capsule having a single outer diameter. As can be seen in the image, the villi in FIG. 19 are generally compressed due to the sides of the capsule 130 pressing against the villi during imaging. FIG. 20 shows data collected from a duodenum region of a patient using a tethered OCT capsule system in which the pill-shaped capsule includes a notch such as that shown in FIG. 18. In FIG. 20, most of the villi 1902 are less compressed and thus are visible, which may facilitate CD diagnosis.

Figure 21:
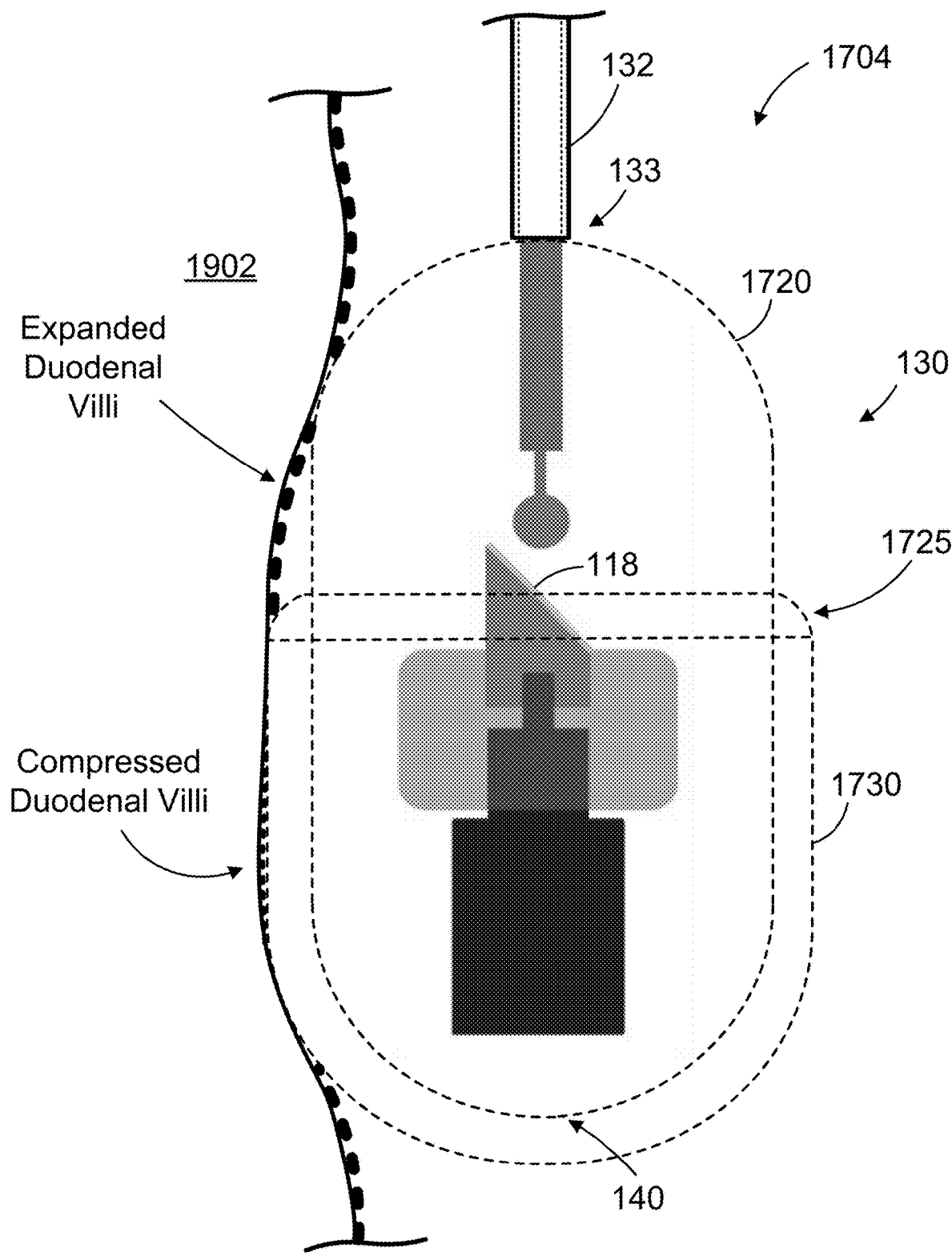
FIG. 21 is a schematic illustration of imaging of a duodenum region using a tethered optical imaging probe with a capsule such as that shown in FIG. 17.
Figure 22:
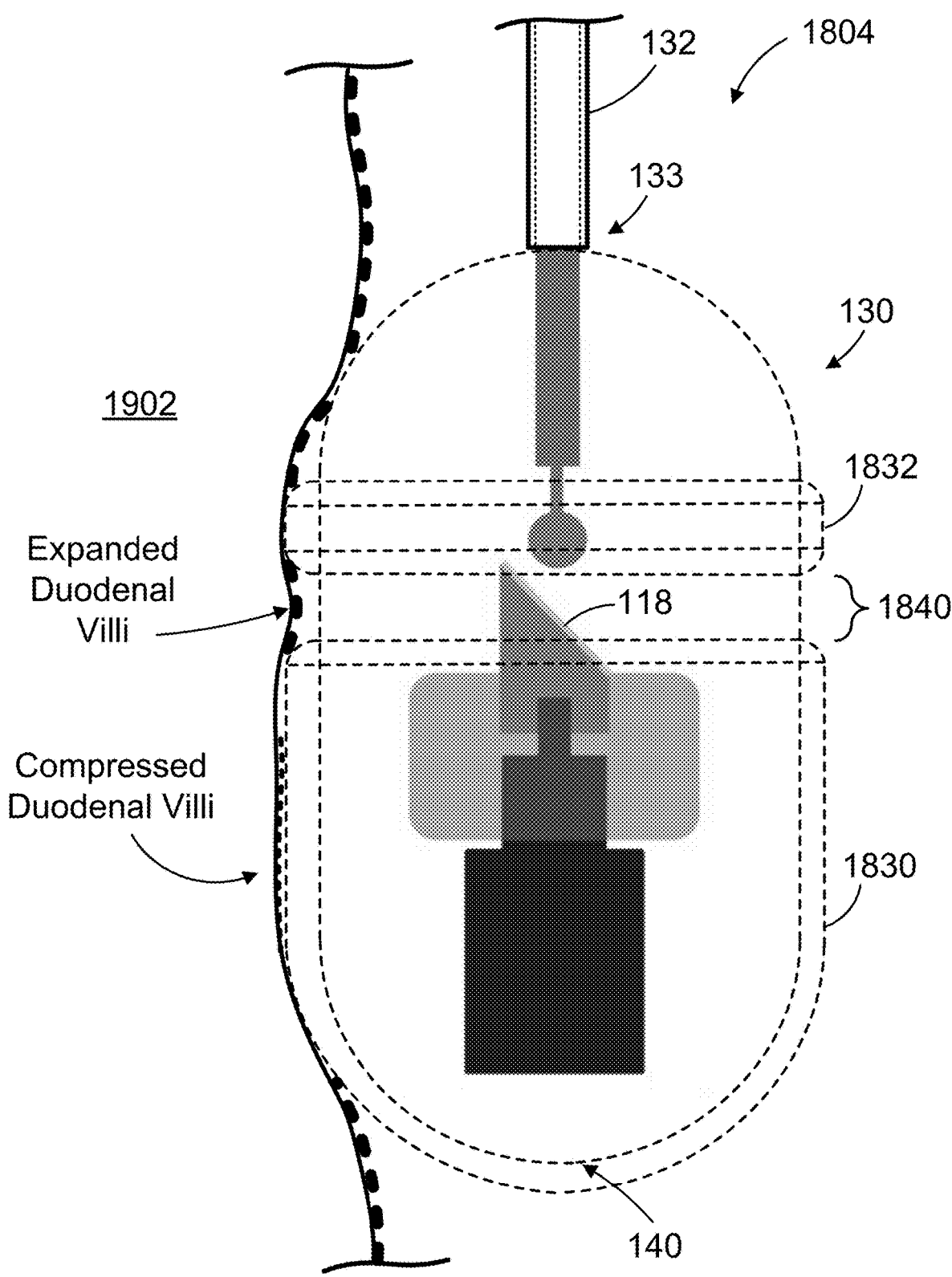
FIG. 22 is a schematic illustration of imaging of a duodenum region using a tethered optical imaging probe with a capsule such as that shown in FIG. 18.

FIG. 21 shows a capsule with a second portion 1730 that has a larger diameter than the rest of the body of the capsule 130. Duodenal villi 1902 are shown along one side of the capsule 130 in FIG. 21, demonstrating how villi are permitted to expand in the smaller-diameter vicinity of the transition region 1725, where imaging data is collected via the reflective surface 118. Similarly, FIG. 22 shows how duodenal villi 1902 are permitted to expand in the region of the notch 1840 to facilitate imaging in a natural, non-compressed condition.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A tethered optical imaging probe, comprising:
a motor;
a reflective surface rotatably coupled to the motor;

a capsule enclosing the motor and the reflective surface, wherein the capsule is dimensioned to be swallowable by a patient; and a tether coupled to a first end of the capsule, the tether including an optical waveguide arranged therein, wherein the optical waveguide is arranged to receive source light at a distal end of the optical waveguide and project the source light from a proximal end of the optical waveguide onto the reflective surface wherein light from the reflective surface is projected onto a target, and wherein the optical waveguide is arranged to receive reflected light from the reflective surface at the proximal end of the optical waveguide and transmit the reflected light toward the distal end of the optical waveguide, at least one wire that extends into and along the capsule, wherein a feedback signal corresponds to the frequency at which light received at the proximal end of the optical waveguide includes information indicative of the presence of the at least one wire; and the tethered optical imaging probe being configured to transmit, using the optical waveguide, the feedback signal that is indicative of a speed at which the motor is rotating as the reflective surface is rotatably positioned by the motor and receive a control signal to control the rotational speed of the motor based on the feedback signal.

2. The tethered optical imaging probe of claim 1, wherein the motor, the reflective surface, and the optical waveguide are positioned to provide a circumferential field of view that encompasses a portion of the capsule.

3. The tethered optical imaging probe of claim 2, further comprising a light emitting material arranged on the portion of the capsule.

4. The tethered optical imaging probe of claim 3, wherein the light emitting material comprises at least one of a phosphorescent material or a fluorescent material.

5. The tethered optical imaging probe of claim 3, wherein the light emitting material is configured to absorb a portion of the source light reflected from reflective surface and subsequently emit signal light at a wavelength different than the source light back to the reflective surface and into the proximal end of the optical waveguide.

6. The tethered optical imaging probe of claim 2, wherein the at least one wire includes a light reflecting material,
wherein the feedback signal corresponds to the frequency at which light reflected by the light reflecting material is received at the proximal end of the at least one optical waveguide.

7. The tethered optical imaging probe of claim 6, wherein the at least one wire that extends into and along the capsule is electrically coupled to the motor.

8. The tethered optical imaging probe of claim 7, wherein the information indicative of the presence of the at least one wire comprises at least one of:
the presence of a shadow in the light received at the proximal end of the at least one waveguide,
the presence of light emitted by the at least one wire in the light received at the proximal end of the at least one waveguide, and
the presence of light reflected by the at least one wire in the light received at the proximal end of the at least one waveguide.

9. The tethered optical imaging probe of claim 1, further comprising a damping weight coupled to a drive shaft of the motor for rotation therewith.

10. The tethered optical imaging probe of claim 1, wherein a periodic control signal is supplied to the motor to control the rotation of the motor.

11. The tethered optical imaging probe of claim 10, wherein the periodic control signal is in the form of a square wave and a duty cycle of the periodic control signal is based on the feedback signal.

12. The tethered optical imaging probe of claim 10, wherein the periodic control signal is in the form of a sine wave and at least one of a DC offset and peak voltage of the periodic control signal is based on the feedback signal.

13. The tethered optical imaging probe of claim 1, wherein the capsule comprises:
a first portion having a first diameter;
a second portion having a second diameter larger than the first diameter; and
a transition portion between the first diameter and the second diameter.

14. The tethered optical imaging probe of claim 13, wherein a field of view of the tethered optical imaging probe encompasses at least a section of the first portion that is adjacent to the transition portion.

15. The tethered optical imaging probe of claim 14, wherein the first diameter is one millimeter smaller than the second diameter.

16. The tethered optical imaging probe of claim 13, wherein the capsule further comprises:
a third portion of the second diameter,
wherein the third portion is spaced apart from the first portion, creating a notch having the first diameter between the third portion and the second portion.

17. The tethered optical imaging probe of claim 16, wherein a field of view of the tethered optical imaging probe encompasses at least a section of the notch.

18. The tethered optical imaging probe of claim 16, wherein the first diameter is 0.5 millimeters smaller than the second diameter, and the notch is two millimeters wide.

19. A tethered capsule endomicroscopy system, comprising:
an optical source arranged to emit source light;
an optical imaging probe including:
a motor;
a reflective surface rotatably coupled to the motor;
a capsule enclosing the motor and the reflective surface, wherein the capsule is dimensioned to be swallowable by a patient; and
a tether coupled to a first end of the capsule, the tether including an optical waveguide arranged therein, wherein the optical waveguide is arranged to receive the source light at a distal end of the optical waveguide and project the source light from a proximal end of the optical waveguide onto the reflective surface wherein light from the reflective surface is projected onto a target, and/or wherein the optical waveguide is arranged to receive reflected light from the reflective surface at the proximal end of the optical waveguide and transmit the reflected light toward the distal end of the optical waveguide;
at least one wire that extends into and along the capsule, wherein a feedback signal corresponds to the frequency at which light received at the proximal end of the optical waveguide includes information indicative of the presence of the at least one wire;
an optical detector arranged to detect the reflected light from the reflective surface transmitted by the optical waveguide; and
a controller configured to:

reconstruct the reflected light detected by the optical detector into cross-sectional morphological data,
receive, using the optical waveguide, the feedback signal that is indicative of a speed at which the motor is rotating, and
generate a control signal to control the rotational speed of the motor based on the feedback signal.

20. A method for controlling a tethered optical imaging probe, the tethered optical imaging probe including a motor, a reflective surface rotatably coupled to the motor, a capsule that is dimensioned to be swallowable by a patient and encloses the motor and the reflective surface, a tether coupled to a first end of the capsule and having an optical waveguide arranged therein, the optical waveguide is arranged to receive source light at a distal end of the optical waveguide and project the source light from a proximal end of the optical waveguide onto the reflective surface wherein light from the reflective surface is projected onto a target, and the optical waveguide is arranged to receive reflected light from the reflective surface at the proximal end of the optical waveguide and transmit the reflected light toward the distal end of the optical waveguide, the method comprising:
outputting source light from the optical waveguide onto the reflective surface;
rotating the reflective surface, via the motor, thereby forming a circumferential optical path formed by the source light output from the optical waveguide onto the reflective surface as the reflective surface is rotated, wherein the detection object is arranged in the circumferential optical path;
transmitting using the optical waveguide a feedback signal each time the reflective surface completes a single rotation, wherein the feedback signal is indicative of a speed at which the motor is rotating; and
controlling a rotational speed of the motor based on the feedback signal,
wherein the capsule comprises a first portion having a first diameter, a second portion having a second diameter larger than the first diameter, and a transition portion between the first diameter and the second diameter, and wherein the circumferential optical path encompasses at least a section of the first portion that is adjacent to the transition portion.

21. The method of claim 20, further comprising:
reflecting, by the reflective surface, the source light onto a plurality of villi in a duodenum of a patient;
reflecting, by the reflective surface, light received from the plurality of villi toward the proximal end of the at least one optical waveguide;
detecting, by an optical detector, reflected light from the plurality of villi transmitted from the reflective surface via the at least one optical waveguide;
generating cross-sectional morphological data based on the reflected light; and
generating, based on the cross-sectional morphological data, an image of the plurality of villi for use in evaluating the length of the plurality of villi to screen the patient for at least one disease or condition that affects villi morphology.

22. The method of claim 21, wherein the at least one disease or condition that affects villi morphology includes at least one of: celiac disease, drug-induced enteropathy, common variable immunodeficiency, small intestine bacterial overgrowth, Crohn's disease, intestinal lymphoma, autoimmune enteropathy, or environmental enteric dysfunction.

23. A tethered optical imaging probe, comprising:
a motor;
a reflective surface rotatably coupled to the motor;
a capsule enclosing the motor and the reflective surface, including:
a first portion having a first diameter;
a second portion having a second diameter larger than the first diameter; and
a transition portion between the first diameter and the second diameter, wherein a field of view of the tethered optical imaging probe encompasses at least a section of the first portion that is adjacent to the transition portion, wherein the capsule is dimensioned to be swallowable by a patient; and
a tether coupled to a first end of the capsule, the tether including an optical waveguide arranged therein, wherein the optical waveguide is arranged to receive source light at a distal end of the optical waveguide and project the source light from a proximal end of the optical waveguide onto the reflective surface wherein light from the reflective surface is projected onto a target, and wherein the optical waveguide is arranged to receive reflected light from the reflective surface at the proximal end of the optical waveguide and transmit the reflected light toward the distal end of the optical waveguide,
the tethered optical imaging probe being configured to transmit, using the optical waveguide, a feedback signal that is indicative of a speed at which the motor is rotating as the reflective surface is rotatably positioned by the motor and receive a control signal to control the rotational speed of the motor based on the feedback signal, wherein a field of view of the tethered optical imaging probe encompasses at least a section of the first portion that is adjacent to the transition portion.

24. The tethered optical imaging probe of claim 23, wherein the first diameter is one millimeter smaller than the second diameter.

25. The tethered optical imaging probe of claim 23, wherein the capsule further comprises:
a third portion of the second diameter,
wherein the third portion is spaced apart from the first portion, creating a notch having the first diameter between the third portion and the second portion.

26. The tethered optical imaging probe of claim 25, wherein the field of view of the tethered optical imaging probe encompasses at least a section of the notch.

* * * * *

UNITED STATES PATENT AND TRADEMARK OFFICE
CERTIFICATE OF CORRECTION

PATENT NO. : 11,147,503 B2
APPLICATION NO. : 15/882557
DATED : October 19, 2021
INVENTOR(S) : Guillermo J. Tearney et al.

Page 1 of 1

It is certified that error appears in the above-identified patent and that said Letters Patent is hereby corrected as shown below:

In the Specification

Column 16, Line 21, "AD" should be --$\Delta D$--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*